(12) United States Patent
Roberts et al.

(10) Patent No.: US 8,688,473 B2
(45) Date of Patent: Apr. 1, 2014

(54) SYSTEM AND METHODS OF PROVIDING PHARMACY SERVICES

(71) Applicant: CVS Pharmacy, Inc., Woonsocket, RI (US)

(72) Inventors: Jonathan C. Roberts, East Greenwich, RI (US); Dimitri G. Betses, Merrimack, NH (US)

(73) Assignee: CVS Pharmacy, Inc., Woonsocket, RI (US)

( * ) Notice: Subject to any disclaimer, the term of this patent is extended or adjusted under 35 U.S.C. 154(b) by 0 days.

(21) Appl. No.: 13/970,708

(22) Filed: Aug. 20, 2013

(65) Prior Publication Data

US 2013/0339048 A1    Dec. 19, 2013

Related U.S. Application Data

(60) Division of application No. 12/813,742, filed on Jun. 11, 2010, now Pat. No. 8,554,581, which is a continuation of application No. 10/816,452, filed on Mar. 31, 2004, now Pat. No. 7,827,041.

(51) Int. Cl.
*G06Q 10/00* (2012.01)
*G06Q 50/00* (2012.01)

(52) U.S. Cl.
USPC .................................. 705/2; 705/3

(58) Field of Classification Search
USPC ....................................... 705/2, 3
See application file for complete search history.

(56) References Cited

U.S. PATENT DOCUMENTS

| | | | |
|---|---|---|---|
| 5,737,539 A * | 4/1998 | Edelson et al. | 705/3 |
| 5,752,621 A * | 5/1998 | Passamante | 221/13 |
| 7,072,737 B2 * | 7/2006 | Lunak et al. | 700/236 |
| 2002/0188469 A1 * | 12/2002 | Shalmi et al. | 705/2 |
| 2003/0115085 A1 * | 6/2003 | Satoh | 705/5 |
| 2003/0149599 A1 * | 8/2003 | Goodall et al. | 705/2 |

* cited by examiner

*Primary Examiner* — Neal Sereboff
(74) *Attorney, Agent, or Firm* — Mintz Levin Cohn Ferris Glovsky and Popeo, P.C.

(57) ABSTRACT

System and methods for processing a drug prescription transaction are configured to identify and resolve any issue or problem associated with the transaction during one or more early stages of processing. System and methods of processing the transaction handle prescription and customer data entry, pharmacy inventory check, prescription refill authorization check and/or insurance adjudication review well in advance of production and quality assurance stages by identifying and resolving any issue or problem. Prescription fulfillment is prioritized and estimated prescription pick-up times are predicted based on one or more outcomes of such early stage processing. Customers can be provided with realistic and relatively accurate prescription pick up times that a pharmacy can efficiently and consistently meet as a result of fulfillment prioritization. Further, system and methods for determining a staffing schedule for a workflow process requiring different skill levels during different operation times is provided.

8 Claims, 11 Drawing Sheets

470

ESTIMATED WAIT TIME TABLE:

471

| # OF RELEVANT SCRIPTS IN QUEUES | # OF SCRIPTS IN ORDER | | | | | | | | | |
|---|---|---|---|---|---|---|---|---|---|---|
| | 1 | 2 | 3 | 4 | 5 | 6 | 7 | 8 | 9 | 10+ |
| 0 | 10 | 10 | 15 | 15 | 15 | 20 | 20 | 25 | 25 | 25 |
| 1 | 10 | 10 | 15 | 15 | 15 | 20 | 20 | 25 | 25 | 25 |
| 2 | 10 | 10 | 15 | 15 | 15 | 20 | 20 | 25 | 25 | 25 |
| 3 | 10 | 10 | 15 | 15 | 15 | 20 | 20 | 25 | 25 | 25 |
| 4 | 10 | 15 | 15 | 15 | 15 | 20 | 20 | 25 | 25 | 25 |
| 5 | 15 | 15 | 15 | 15 | 15 | 20 | 20 | 25 | 25 | 25 |
| 6 | 15 | 15 | 15 | 15 | 20 | 20 | 20 | 25 | 25 | 25 |
| 7 | 15 | 15 | 15 | 20 | 20 | 20 | 20 | 25 | 25 | 25 |
| 8 | 15 | 15 | 20 | 20 | 20 | 20 | 20 | 25 | 25 | 25 |
| 9 | 15 | 20 | 20 | 20 | 20 | 20 | 25 | 25 | 25 | 25 |
| 10 | 20 | 20 | 20 | 20 | 20 | 25 | 25 | 25 | 25 | 25 |
| 11-12 | 20 | 20 | 20 | 25 | 25 | 25 | 25 | 25 | 30 | 30 |
| 13-14 | 20 | 25 | 25 | 25 | 25 | 25 | 30 | 30 | 30 | 30 |
| 15-16 | 25 | 25 | 25 | 25 | 30 | 30 | 30 | 30 | 30 | >30 |
| 17-22 | 30 | 30 | 30 | 30 | 30 | 30 | >30 | >30 | >30 | >30 |
| 23+ | >30 | >30 | >30 | >30 | >30 | >30 | >30 | >30 | >30 | >30 |

SYSTEM AND METHODS OF PROVIDING PHARMACY SERVICES

PRIOR APPLICATIONS

This application is a divisional of U.S. application Ser. No. 12/813,742 filed Jun. 11, 2010, which is a continuation of U.S. application Ser. No. 10/816,452 filed Mar. 31, 2004, the contents of which is hereby incorporated by reference.

FIELD OF THE INVENTION

The invention relates to providing pharmacy services for drug prescription fulfillment.

BACKGROUND OF THE INVENTION

Customer service has become a main focus and an important means by which many commercial service providers, such as banks, insurance companies, hospitals and retailers, distinguish themselves and remain competitive in their respective markets. Service providers attempt to gain new customers and to retain existing customers by providing and improving service that meets the needs and expectations of their customers. Pharmacies are not immune to competition and similarly rely upon providing and improving customer service to retain and expand customer bases. Data show that a major reason for a customer to switch from one pharmacy to another for such services as drug prescription fulfillment is due to dissatisfaction with the quality of service that a pharmacy provides. In particular, pharmacy service issues are cited as a major reason for substantial loses in annual revenue from prescription sales.

Pharmacy service issues can result from a number of problems that pharmacies and customers experience that can range from a lack of personnel at pharmacy service counters to a lack of adequate communication between pharmacies and customers concerning any problems that cause prescriptions to be delayed, only partially filled or not filled at all. As a result, pharmacies cannot meet customers' needs and expectations, for instance, with respect to promised prescription pick-up times.

Many pharmacies do not attempt to account for the root causes of service issues. For example, a large percentage of drug prescriptions can develop into problem transactions due to, for instance, insurance rejection, lack of pharmacy inventory or lack of authorization for prescription refill. Problems transactions can require separate processes for resolution outside of prescription fulfillment processes. As a result, problem transactions have a tremendous impact on customer service by interrupting the workflow of prescription fulfillment and removing pharmacy staff from dedicated responsibilities. When pharmacy staff are removed from fulfillment processes and attempt to resolve problem transactions, such as by contacting a third party including an insurance provider or a doctor, any grouping of prescriptions to be filled and/or any prioritization of prescription fulfillment can often be destroyed and can cause delayed or no prescription fulfillment. As a result, a pharmacy cannot provide service that meets customers' needs and expectations, especially at pick-up when customers anticipate their prescriptions have been properly processed and are available.

As noted above, prescription fulfillment processes generally are not designed to handle problem transactions. Such processes often do not surface issues or problems early enough during prescription processing to allow sufficient time for resolution. Prescription fulfillment processes also encourage pharmacy staff to pass problems along rather than to attempt resolution because no clear protocols or procedures are provided to resolve specific issues and problems. In addition, members of pharmacy staff typically are not specifically assigned or dedicated to resolving problem transactions and are often involved in multiple tasks at different stages of prescription fulfillment. As a result, pharmacy staff can have difficulty in organizing prescriptions, maintaining priority of fulfillment and preventing unfilled prescriptions from accumulating when such tasks are performed along with efforts to resolve issues and problems. Prescription processing thereby becomes inefficient and inconsistent and can significantly impact customer service.

Resolution of problem transactions, therefore, can become complex and time-consuming, and can require a number of pharmacy staff, which often reinforces problems and/or causes additional problems, such as those noted, including unfilled prescription accumulation. In addition, pharmacy information systems often are not fully or properly used to uncover issues and problems and to enable resolution during early stages of processing in order to minimize/eliminate customer service problems.

Further, pharmacy workflow often neglects or does not adequately staff pharmacy/customer interfaces. For example, pharmacies rarely call customers in advance of pick-up times to inform customers of issues or problems associated with fulfilling their prescriptions. Customers, therefore, are not aware of any problems until customers attempt to pick up their prescriptions. Also, pharmacies often do not staff services for prescription intake and pick-up with persons having the skills and experience to explain problem transactions and/or to attempt resolution. In particular, pharmacy staff providing pick-up and cashiering services often must attempt to provide customers with explanations for problem transactions. Typically, such persons are ill informed and the least capable people to explain issues and problems to customers. Customer service thereby can be further impacted and cause significant customer dissatisfaction.

Thus, systems and methods of drug prescription fulfillment are desired that resolve at least some of the issues and problems associated with prescription processing and strive to meet customer needs and expectations.

SUMMARY OF THE INVENTION

In general, in one aspect, the invention provides a workflow management method for processing a drug prescription in a pharmacy comprising receiving a drug prescription, estimating a date and a time by which the drug prescription will be fulfilled and available to a customer, initiating a prescription transaction by retrieving data from the drug prescription, checking the pharmacy inventory, obtaining an insurance adjudication review, and predicting a prescription pick up time. The predicted prescription pick up time is determined by one of confirming the estimated date and time and resetting the estimated date and time by which the drug prescription will be fulfilled and available to the customer.

In another aspect, the invention provides a computer readable memory having a computer program for controlling workflow for processing a drug prescription in a pharmacy comprising recording an estimated date and a time by which the drug prescription will be fulfilled and available to a customer after receipt of a drug prescription, initiating a prescription transaction by retrieving data from the drug prescription, checking the pharmacy inventory, obtaining an insurance adjudication review, and predicting a prescription pick up time. The predicted prescription pick up time being determined by one of confirming the estimated date and time and resetting the estimated date and time by which the drug prescription will be fulfilled and available to the customer; and recording the predicted prescription pick up time.

In a further aspect, the invention provides a workflow management system for controlling the fulfillment of a drug prescription comprising one or more workflow stations established to complete a series of pharmacy activities to fulfill the drug prescription, each workflow station handling one or more specific tasks. Each workflow station is defined in terms of one or more responsibilities of one or more persons staffing the workflow station and is further defined in terms of one or more skill levels required to handle the specific tasks of each workflow station. Each workflow station is assigned a minimum number of persons required at each skill level, the minimum number of persons required at each skill level being a number predicted from data related to volume and timing of one or more of the pharmacy activities.

In an additional aspect, the invention provides a method for determining a staffing schedule for assigning persons to a transaction workflow comprising generating a predicted volume of transactions for a period of time to be scheduled, generating a predicted timing of the predicted volume of transactions for the period of time, and expressing the predicted timing as a predicted volume of transactions for each of specific increments of time within the period of time to be scheduled. The method further comprises converting the predicted volume of transactions for each of the specific increments of time into a recommended minimum number of persons required at one or more skill levels, and producing a recommended staffing schedule for the period of time that represents the recommended minimum number of persons required at each skill level for each of the specific increments of time.

In still a further aspect, the invention provides a computer readable memory having a computer program for determining a staffing schedule for assigning persons to a transaction workflow comprising generating a predicted volume of transactions for a period of time to be scheduled, generating a predicted timing of the predicted volume of transactions for the period of time, and expressing the predicted timing as a predicted volume of transactions for each of specific increments of time within the period of time to be scheduled. The method further comprises converting the predicted volume of transactions for each of the specific increments of time into a recommended minimum number of persons required at one or more skill levels, and producing a recommended staffing schedule for the period of time that represents the recommended minimum number of persons required for each skill level for each of the specific increments of time.

Various aspects of the invention may provide one or more of the following advantages. A drug prescription transaction can be processed such that identification and resolution of any issue or problem associated with the transaction occur at one or more early stages of processing. A method of processing a drug prescription can define one or more early processing stages, including prescription drop-off at a pharmacy, prescription and customer data entry into a pharmacy's information system, pharmacy inventory check, prescription refill authorization and/or insurance adjudication review that are conducted as soon as possible after a pharmacy receives a drug prescription. Complex issues or problems can typically arise during these early stages that can affect processing of the prescription transaction and, if identified during any of such early processing stages, can be resolved well in advance of other stages of processing to help to provide satisfactory customer pick-up times that can meet customer expectations.

During any or all of the early processing stages described, a pharmacy can remain in communication with a customer in order to inform the customer of any issue or problem associated with a transaction that is identified and to inform the customer of efforts the pharmacy can take to resolve the issue or problem and the time estimated for resolution. At the outset, a customer can request a prescription pick-up time or can be given an estimated prescription pick-up time that a pharmacy provides during initiation of the prescription transaction, such as during data entry. After prescription and customer data are entered into a pharmacy's information system, pharmacy inventory is checked, prescription refill authorization is checked and/or an insurance adjudication review is performed, the pharmacy either can confirm or reset the customer's requested estimated pick-up time or the pharmacy's estimated pick-up time in view of any issue or problem that may have been identified in order to provide the customer with a confirmed or reset estimated prescription pick-up time. The confirmed or reset estimated pick-up time provides the customer with a relatively accurate and realistic estimated prescription pick-up time that the pharmacy can likely meet in view of any issue or problem that needs to be or has been resolved. A customer's expectations can thereby be set and reset according to the results or outcome of the processing activities conducted during the early stages of processing. An estimated pick-up time, e.g., customer requested or pharmacy designated pick-up time, can also take into account the steps and time required for resolution of the issue or problem prior to prescription fulfillment.

A drug prescription can enter a pharmacy work queue and can be prioritized for fulfillment according to a customer requested pick-up time or a pharmacy estimated customer pick-up time, as described above. The prescription pick-up time can be provided directly to a customer during early stages of processing when the pharmacy is in communication with the customer, e.g., at service drop-off workstation. In addition, a prescription pick-up time can be provided by a default pick-up time determined by a pharmacy for those prescriptions that are "dropped-off" via a pharmacy's voice response system (voice mail), or facsimile, or other method of providing a drug prescription to a pharmacy that does not indicate a required or desired customer pick-up time.

In addition, a drug prescription can be further prioritized for fulfillment in a work queue according to whether a customer will wait for his/her prescription to be filled such that the prescription is given priority with respect to fulfillment relative to other outstanding prescriptions. Such drug prescriptions can be highlighted during processing, e.g., identified as a "waiter" by any of a number of different means to alert pharmacy staff of a customer waiting for a prescription to be fulfilled.

Drug prescription transactions can be processed using a multiple of workstations wherein each workstation accomplishes specific tasks toward prescription fulfillment. Such workstation tasks can be defined in terms of the roles and responsibilities and the requisite skill level of each person who staffs a workstation. The roles and responsibilities of each workstation can outline specific protocols by which a staff person can attempt to resolve an issue or problem associated with a transaction, depending on the nature of the issue or problem and the steps and time required to resolve the issue or problem. A multiple of workstations can be configured and arranged in a pharmacy to help to minimize customer wait times and customer drop-off/pick-up lines, e.g., at customer service workstations dedicated for prescription drop-off and pick-up. In addition, a multiple of workstations can be configured and arranged that is conducive to a stage-by-stage or compartmentalized process or workflow and helps staff persons manning the workstations to meet the tasks required at each workstation.

Issue and problem resolution can be accounted for using an action note, whereby the steps taken for resolution and the outcome of such steps are documented. In addition, communication with a customer regarding identification and resolution of an issue or problem can be documented using an action note. An action note can be affixed to a prescription label and/or receipt used to process a prescription such that a history of any issue or problem associated with the transaction remains with the prescription through various stages of processing to provide pharmacy staff and, ultimately, a customer with information about the transaction and any resolution of the associated issue or problem.

A process and associated software program can be provided that are designed and configured for determining and implementing an appropriate staffing schedule for a pharmacy that helps to provide optimal staffing coverage for various pharmacy activities. Such a scheduling process and software can use pharmacy-specific data and/or chainwide data from a multiple of pharmacy stores in a given geographical region to predict the nature, the timing and/or the volume of specific pharmacy activities. For instance, data for specific store activities can include, but are not limited to, a number of new prescriptions dispensed per hour and a number of refill prescriptions dispenser per hour in a pharmacy store (pharmacy-specific data). Data such as average rates of insurance and refill authorization problems that occur in a single pharmacy or in a multiple of pharmacy chain stores (chainwide pharmacy data) can be used as well to render timing and volume predictions. The process and software program can convert the predicted timing and volume of pharmacy activities into a recommended minimum number of persons required at each skill level for each hour of a given day to be scheduled. In addition, the process and software program can produce a recommended skeleton staffing schedule that indicates the minimum number of persons required at each skill level, e.g., pharmacist, technician and support staff, for each hour of the day. The process and software program can compare the skeleton schedule with an actual schedule, e.g., a prior schedule, to uncover staffing surpluses and deficiencies per hour. Such surpluses and deficiencies can be provided in a report that a scheduler can use to adjust a daily and weekly schedule to thereby minimize/reduce the staffing surpluses and deficiencies. The program can generate from the gap/surplus report a model staffing schedule from which pharmacy staff can be scheduled.

These and other advantages of the invention, along with the invention itself, will be more fully understood after a review of the following figures, detailed description, and claims.

BRIEF DESCRIPTION OF THE DRAWINGS

FIG. 4A is a schematic Estimated wait time table used in the method shown in FIG. 4;

FIG. 8 is a schematic diagram of an existing staffing schedule according to the method shown in FIG. 5;

DETAILED DESCRIPTION OF PREFERRED EMBODIMENTS

Figure 1:
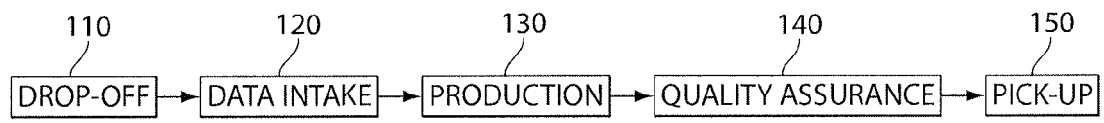
FIG. 1 is a flow diagram of stages of prior art methods of processing drug prescriptions.

Embodiments of the invention provide an improved system and methods for providing pharmacy services and associated customer service. More particularly, embodiments of the invention provide a system and methods of processing drug prescriptions. In at least one embodiment, the invention provides a system and method of multiple workstations for processing and fulfilling drug prescriptions wherein one or more workstations perform one or more stages involved in processing prescriptions. Each workstation is designated, and, optionally, is configured, to accomplish one or more tasks. Workstation tasks can be defined in terms of the roles and responsibilities, as well as the skill levels required, of persons who staff each workstation. Further, workstation tasks can be further defined to limit or focus pharmacy staff-customer interfaces whereby a designated workstation is limited or focused to one or more specific pharmacy-customer interfaces such as, for instance, walk-in drop-off workstations can be limited to interacting with walk-in customers, while drive-thru workstations can be limited to interacting with drive-thru customers. In addition, definition of workstation tasks can be directed to limiting staff to a single or primary pharmacy-customer interface of a workstation to ensure effective customer communication and efficient workflow.

The designated workstations and defined tasks help to create a stage-by-stage process or a compartmentalized workflow whereby each processing stage is handled and/or completed at one or more workstations by one or more staff persons having the requisite skill level, e.g., registered pharmacist (RPh), certified or otherwise trained technician (CT), a customer support associate (CSA) or other support person. In addition, the workstations and tasks are so defined to help to permit early detection and resolution of issues or problems that can occur during processing. Further, the defined workstations and tasks help to ensure pharmacy communication with customers concerning prescription problems and help a pharmacy to provide customers with relatively accurate prescription pick-up times that meet customers' needs and expectations. In part, the invention uses real-time prioritization with respect to prescription fulfillment whereby the actual times when fulfilled prescriptions are promised for customer pick-up are used to manage and to prioritize pharmacy workflow. Real-time prioritization can further take into account whether a customer will wait for his/her prescription to be fulfilled or will return to the pharmacy at a later time to pick-up the fulfilled prescription in order to further manage and prioritize workflow. The system and methods according to the invention thereby provide an efficient and streamlined process for fulfilling drug prescriptions in a timely manner, while minimizing/eliminating the impact of issues and problems associated with processing drug prescriptions.

The invention further provides a method for determining and implementing schedules to staff the multiple workstations with a sufficient number of persons having the requisite skill levels to handle and/or to complete each workstation's tasks. Embodiments of the scheduling method according to the invention use pharmacy operations data to predict the timing and the volume of pharmacy activities and to produce a model schedule from which persons may be scheduled to ensure sufficient and skilled staff are available to handle all pharmacy activities. Other embodiments are within the scope of the invention.

Referring to FIG. 1, a flow diagram is provided that illustrates at least some of the stages of prior art methods 100 of processing drug prescriptions. Typically, prior art methods include one or more stages of drop-off 110 or submitting a drug prescription to a pharmacy, data intake 120 or obtaining prescription and customer information, production 140 or dispensing drugs according to prescriptions, quality assurance 140, and pick-up 150 or providing the fulfilled prescription to a customer or an agent for a customer. The methods 100 represented in FIG. 1 do no necessarily proceed along the sequence of stages as shown. Within each of these stages, a number of complex issues and problems can arise during processing of drug prescriptions that can significantly affect the quality and the efficiency with which prescriptions are fulfilled and dispensed to customers. Embodiments of the system and methods according to the invention are configured and implemented to address many of these issues and problems and to resolve such issues and problems at early stages of processing to help to ensure efficient and timely prescription fulfillment and to enhance customer service.

Figure 2:
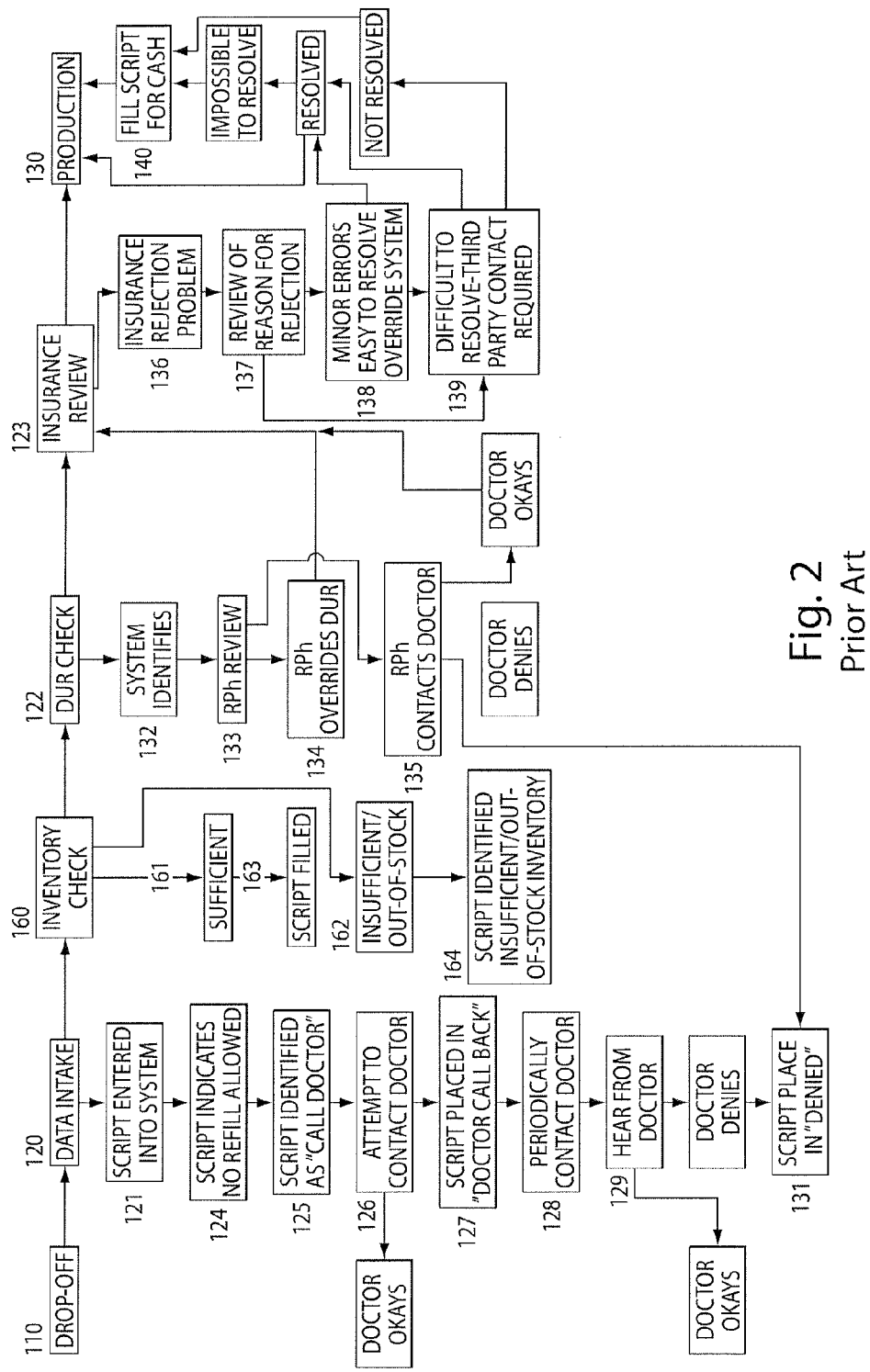
FIG. 2 is a schematic flow diagram of resolving issues and problems that can arise during processing of drug prescriptions.

Referring to FIG. 2, a schematic flow diagram illustrates a number of issues and problems that occur at one or more stages of drop-off 110 and at one or more stages of data intake 120 and steps taken to resolve issues and problems. According to prior art methods, a customer typically submits a drug prescription to a pharmacy, e.g., by hand, by telephone, by leaving a voice mail message on a pharmacy voice response system, by faxing the prescription to the pharmacy, and/or by the customer's prescriber/doctor telephoning or faxing the pharmacy to "call-in" the prescription. After submission of the prescription to the pharmacy, communication or contact between these parties is typically terminated.

The prescription then proceeds from drop-off 110 to one or more data intake stages 120 whereby a pharmacy obtains prescription and customer information, e.g., health insurance information. At one or more stages of processing according to prior art methods, and in particular at stages of drop-off 110 and data intake 120, different types of complex problems can arise that can delay and/or interfere with or otherwise affect fulfillment of prescriptions. Prior art methods are not configured and/or implemented to discover such issues and problems associated with prescription transactions during early stages of processing, and often tend to ignore issues and problems entirely. In addition, prior art methods do not communicate the occurrence of such issues and problems to customers when such issues and problems arise during processing. In many cases, such lack of communication between pharmacy and its customers is due to little or no emphasis prior art method place on pharmacy-customer interfaces, e.g., opportunities for customer communication, such as at drop-off and pick-up service counters.

Problems associated with prescription transactions can interrupt the overall pharmacy workflow and often require pharmacy personnel to be removed from dedicated responsibilities to resolve such problems. For instance, at drop-off and data intake stages 110 and 120, an initial interview between a pharmacy and a customer or prescriber's/doctor's office, can fail to obtain critical information and/or can obtain incomplete information. For these reasons, first-time prescriptions are particularly vulnerable at the drop-off and data intake stages 110 and 120. In addition, prescriptions "called-in", e.g., via voice mail messages and faxes, can provide inaccurate and/or incomplete information. A lack of or incomplete information can cause either a delay in or an inability to successfully process a prescription, which can result in a pharmacy not meeting customers' expectations, especially with respect to promised prescription pick-up times. Other issues and problems can occur, such as a lack of sufficient inventory and a lack of authorization to refill an existing prescription that can cause delay in or prevent successful processing of a prescription.

In addition, drop-off and data intake stages 110 and 120 are susceptible to human error whereby pharmacy personnel manning a drop-off/data intake area, e.g., a service counter, a telephone, a fax machine, a telephone voice response system or a drive-thru window, can provide erroneous and/or incomplete information to customers. In particular, pharmacy personnel can arbitrarily assign a time within which a prescription will be filled and available for a customer to pick-up and can thereby provide the customer with an erroneous and/or over-promised time within which the prescription will be available. Pharmacy personnel working within prior art methods typically do not have a consistent basis, guidelines or other information for assigning a pick-up time and often estimate a pick-up time, for instance, without first checking a pharmacy's inventory of a particular drug or whether a prescription permits a refill. In addition, in other instances, pharmacy personnel can provide a customer with an estimated and/or arbitrarily assigned pick-up time before a pharmacy obtains and confirms necessary prescription and customer information and before a prescription has undergone insurance adjudication and a drug utilization review (DUR), as discussed below in further detail. Thus, a customer can drop-off a prescription and a pharmacy can quote an inaccurate pick-up time as a result of one or more problems that occur during processing. Typically, the inaccuracy of an estimated pick-up time and/or any problems associated with processing a prescription do not become known to a pharmacy or a customer until the customer actually attempts to pick-up his/her prescription. At this point, resolution of any problems may be too late to permit the pharmacy to meet the customer's expectations with respect to pick-up time and service. In addition, any problems and efforts to resolve such problems typically cause prescription processing and workflow to become inefficient or inconsistent.

As shown in FIG. 2, stages of data intake 120 typically involve at least four general areas of prescription processing, prior to stages of production 130, during which complex issues and problems can occur that often require resolution before a prescription can be further processed and successfully fulfilled. These areas include entering data 121 related to a drug prescription and customer information into a pharmacy's information processing system, e.g., a networked computer system comprised of one or more operatively connected computers, checking a pharmacy inventory for stock 160, conducting a drug utilization report or DUR check 122, and performing insurance adjudication review 123. As shown in FIG. 2, issues and problems that arise during data intake 121, inventory check 160, DUR check 122 and insurance adjudication review 123 can require pharmacy personnel to take several steps and to make considerable effort to resolve before prescriptions can be fulfilled. Resolution can take from a few minutes up to several days and can involve a number of pharmacy personnel. Without established protocols and guidelines that designate the staff and steps for problem resolution, problem resolution can add significant complexity to prescription processing and can cause problem resolution to be inefficient and inconsistent.

As shown in FIG. 2, for instance, when a pharmacy obtains and enters a prescription into a pharmacy's processing system 121, the system can provide feedback that the prescription cannot be refilled 124. A "no refill" status must be resolved before the prescription can be further processed and filled. A number of steps are typically undertaken within prior art methods to resolve this issue including identifying the prescription 125 to alert pharmacy personnel that a prescriber/doctor who provided the original prescription must be contacted. Thereafter, attempts are made to contact the prescriber/doctor 126. An initial attempt to contact the prescriber/doctor may not be successful and the prescription is identified as a "doctor call-back" 127, which requires periodically contacting the prescriber/doctor 128 until a decision is obtained from the prescriber/doctor 129. In the event the prescriber/doctor denies the refill prescription, the prescription is identified as a "denied" prescription 131. Without an established protocol and staff specifically assigned to handle "no refills", such prescriptions can often end up languishing at the data intake stages 120, which can cause prescriptions to be filled late or not at all. A customer is often not aware of a "no-refill" or other status of his/her prescription before a pick-up time quoted by a pharmacy and does not learn of such a problem until he/she attempts to pick-up a fulfilled prescription from the pharmacy. Customer expectations, therefore, are not met and can result in significant customer dissatisfaction. In the event a prescriber/doctor approves the refill prescription, the prescription can then proceed to one or more stages of DUR check 122, insurance adjudication review 123 and production 130. However, sufficient time may not be available to prepare the prescription for customer pick-up at a promised pick-up time that pharmacy personnel quoted earlier to a customer during drop-off 110.

With further reference to FIG. 2, a pharmacy inventory is checked 160 to confirm whether sufficient volume is currently in inventory to fulfill the prescription. Typically, a pharmacy's information processing system will indicate whether a drug inventory is sufficient 161, or is insufficient or out-of-stock 162. In the event the system indicates the stock is sufficient, the prescription is filled 163 accordingly. In the event the system indicates an insufficient stock or out-of-stock status 162, the prescription is not fulfilled or only partially fulfilled. However, in either case, prior art methods typically do not contact the customer concerning the insufficient stock or out-of-stock status of the prescription. In many instances, the prescription can be identified as being out-of-stock or having insufficient stock 164, but resolution of the stock situation is ignored and communication of the stock status to other pharmacy personnel or the customer is lacking such that the inventory problem does not become known to pharmacy personnel and the customer until the customer attempts to pick-up his/her fulfilled prescription.

Still referring to FIG. 2, each prescription undergoes a DUR check 122. After or in conjunction with a pharmacy entering prescription information into its processing system at data intake stages 120, the pharmacy typically conducts a DUR review 122 to ensure proper drug dose, etcetera, and to confirm whether any adverse drug interactions may exist between the prescribed drug and any other drugs a customer is taking. In the event a DUR check 122 registers an issue 132, e.g., the pharmacy's processing system flags the issue, e.g., a negative DUR such as an incorrect dose or an adverse drug interaction, a registered pharmacist (RPh) must become involved to review the DUR 133 and to either override the issue or negative DUR 134 in the pharmacy's system or contact a prescriber/doctor 135 for further consultation. Typically, an RPh's involvement occurs during the data intake stages 120 and causes the RPh to be drawn from his/her primary responsibilities, e.g., production and/or quality assurance, which can result in delays in dispensing prescriptions. In addition, resolution of an issue or negative DUR check can take a few minutes to a few days to resolve and can thereby significantly impact a pick-up time that pharmacy personnel quoted previously to a customer. In the event an RPh is unsuccessful in contacting a prescriber/doctor during an initial attempt, the prescription can be identified as "doctor call-back" 127, which requires an RPh to periodically attempt to contact the prescriber/doctor 128 until resolution is attained. Typically, a customer is not aware of such an issue or negative DUR check until he/she attempts to pick up the prescription.

In addition, insurance adjudication review 123 can cause complex issues that impact processing of prescriptions. As shown in FIG. 2, a common problem associated with prescription transactions is insurance rejection 136. A customer's insurance can reject a prescription for a number of reasons including policy cancellation, no refill authorized or prior authorization is required from an insurance provider. Upon rejection, pharmacy personnel must review reasons for insurance rejection 137, and attempt to overcome such problems either by overriding the insurance rejection through a pharmacy's processing system 138 or resolving issues causing the rejection 139. Often insurance rejections are caused by minor issues, such as an incorrect name spelling, birth date, or insurance policy number, and can be readily resolved by any staff person by overriding the pharmacy's processing system 138. Other insurance problems are more complex or difficult to resolve that can only be handled by contacting a third party 139, such as a prescriber/doctor, who wrote the prescription, or an insurance provider, to identify the causes for rejection. In other instances in which the prescription is not covered by the customer's insurance, the prescription is processed as a cash transaction typically without the customer's knowledge.

Prior art methods, as described with reference to FIGS. 1 and 2, typically attempt to process drug prescriptions without addressing actual and potential problems before processing has begun and thereby do not discover problems associated with filling a prescription until well after communication with a customer has terminated and the prescription has been placed in a "queue" for dispensing. In many cases, problems are not resolved and/or do not become known to pharmacy personnel or a customer until the customer attempts to pick-up his/her prescription. As the pharmacy may not be aware of any problems with fulfilling a prescription when it accepts the prescription and quotes the customer an estimated pick-up time, the customer has an expectation that the prescription will be successfully fulfilled and will be available at the quoted pick-up time. Thus, when such problems arise, as those schematically illustrated in FIG. 2, the prescription, for instance, may not filled, may not be available at the quoted pick-up time and/or may be filled as a cash transaction 140, e.g., due to insurance rejection, all of which are not known to the customer prior to pick-up.

Resolution of problem transactions during attempts to fill prescriptions and attempts to pick-up prescriptions results in a disruption of workflow and often requires one or more persons to be pulled from his/her primary responsibilities to resolve such problems. Such a result is due to prior art methods not accounting for the time and the man-hours required to resolve the problems associated with fulfilling drug prescriptions because, in part, such methods do not practice clear protocols for resolving specific problems, such as third party problems that involve contacting a doctor or an insurance provider. Many prior art methods often do not account for efforts and steps pharmacy personnel need to take or have taken to resolve problems. In addition, prior art methods typically do not account for problem resolution in providing customers with estimated pick-up times or in offering lead-times, for instance, for telephone and fax call-ins or drive-thru prescription drop-offs. Nor do prior art methods prioritize prescription fulfillment with respect to when prescriptions are dropped off, but rather prioritize fulfillment according to promised pick-up times. Further, prior art methods do not typically distinguish between those customers who choose to wait for his/her prescription and those who choose to return to a pharmacy at a later time for pick-up. In particular, prior art methods rarely notify or require pharmacy personnel to notify a customer in advance of a promised pick-up time if any problems associated with a transaction occur or cannot be resolved. As a result, promised prescription pick-up times can be unrealistic and erroneous, and can cause considerable customer dissatisfaction with a pharmacy's services.

Figure 3:
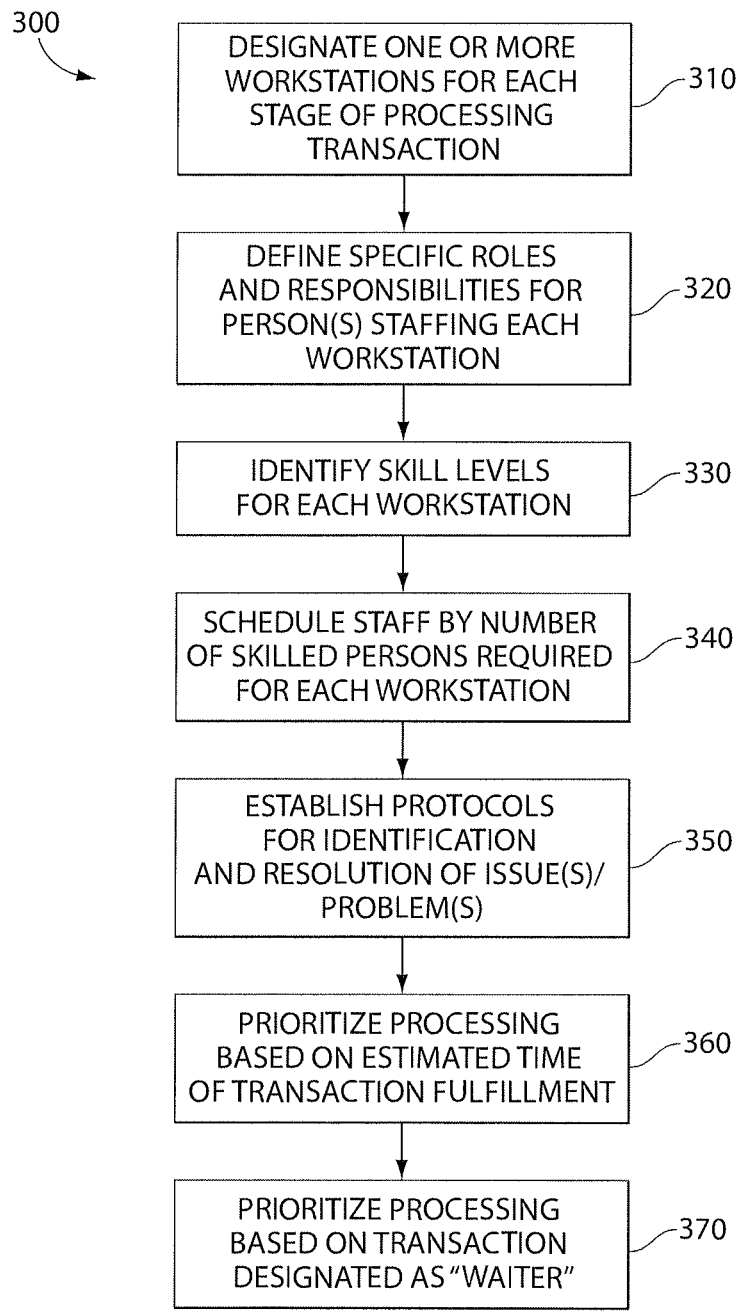
FIG. 3 is a flow diagram of stages of a method of managing a workflow according to the invention.

Referring to FIG. 3, the invention provides a workflow management system and method 300 for providing pharmacy services that is configured and implemented to help to address at least some of the issues, problems and/or other aspects of prescription fulfillment services as described above with reference to FIGS. 1 and 2. The system and method 300 are exemplary and not limited to the stages disclosed, and anticipate that the system and method 300 can be altered or modified, e.g., stages removed, added and/or rearranged, to achieve similar objects of the invention, as will be described below in further detail.

In addition, the method 300, as described herein, can be implemented via a computer software program wherein a computer readable memory, e.g., random access memory (RAM), read only memory (ROM), volatile memory and/or magnetic, electro optical and/or one or more other storage memory devices, includes the software program for implementing and managing the method 300 according to the invention. The computer readable memory can be incorporated with one or more computing devices including, for instance, a mainframe computer, a personal computer, a laptop computer, an Internet appliance, a workstation, an interconnected group of computers and/or any other device(s) configured to help to implement and manage the system and method 300 described herein.

Generally, in an aspect, the workflow management system and method 300 according to the invention comprises designating one or more workstations for each stage of processing 310, e.g., including designating one or more workstations for prescription drop-off and prescription and customer data entry into a pharmacy's processing system, one or more workstations for production, one or more workstations for quality assurance and one or more workstations for customer pick-up. The method 300 also includes defining the roles and responsibilities for persons staffing each workstation 320. In particular, the roles and responsibilities for persons staffing one or more workstations, e.g., for prescription drop-off and prescription and customer data entry are defined such that issues and problems associated with transactions are identified and resolved during these early stages of processing and prior to later stages, e.g., of production 130. Such roles and responsibilities can account for such pharmacy activities as data intake 120, inventory check 160, DUR check 122 and/or insurance adjudication review 123, as described above. In addition, the method 300 includes identifying the skill levels required for each workstation 330 to thereby establish the tasks of each workstation and each person who staffs a workstation. The method 300 also includes scheduling staff by determining a minimum number of persons required at each skill level for each workstation 340 during specific hours of a day and specific days of a week, as will be described below in further detail with reference to FIGS. 5-9. The method 300 includes establishing protocols for data entry and for initiating resolution of problems and issues 350 that can arise during processing. The method 300 also includes prioritizing fulfillment of drug prescriptions based on promised prescription pick up times, e.g., customer requested pick-up time or pharmacy estimated pick-up time. In addition, the method 300 further includes prioritizing fulfillment of drug prescriptions based on whether prescriptions are designated "waiters" 370, e.g., those prescriptions that customers will wait to be filled.

Those of ordinary skill in the art will appreciate that the workflow management system and method 300 according to the invention can be applied in contexts other than providing pharmacy services in which workflow proceeds and/or is managed as a stage-by-stage or compartmentalized process, and, in particular, requires different levels of skill.

Figure 4:
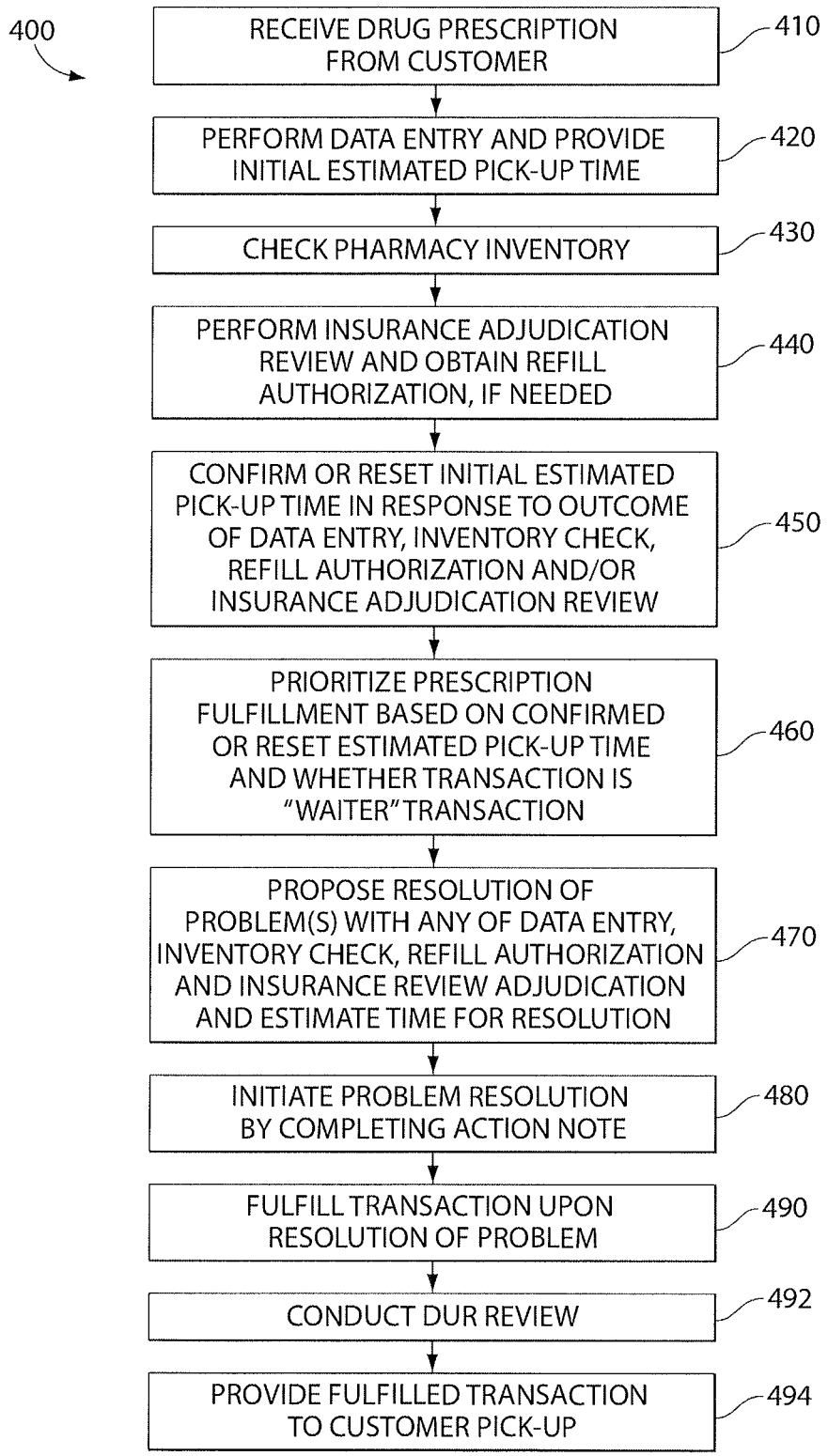
FIG. 4 is a flow diagram of stages of a method of processing a drug prescription according to the invention.

Referring to FIG. 4, and with further reference to FIG. 3, the workflow management system and method according to the invention will be described in further detail in the context of a system and method 400 of processing a drug prescription. The system and method 400 of processing a drug prescription is configured to identify a problem or issue associated with the prescription transaction during early stages of processing, such as during data entry, and to emphasize immediate or prompt initiation of transactions to include the transactions in one or more work queues as soon as possible. The system and method 400 are exemplary and not limited to the stages disclosed, and anticipate that the system and method 400 can be altered or modified, e.g., stages removed, added and/or rearranged At stage 410, a pharmacy receives a drug prescription, e.g., at drop-off workstation. In many cases, a customer typically enters a pharmacy and hands his/her prescription to a staff person at a service counter that serves as a drop-off workstation. The system and method 400 according to the invention can provide two or more dedicated drop-off workstations to minimize/avoid long lines of customers dropping off prescriptions and/or extended waiting periods for the prescriptions to undergo data entry and/or other processing. A customer can also "drop-off" a prescription at a pharmacy by telephoning the pharmacy and providing prescription information verbally to a staff person, or by leaving a voice mail message with a pharmacy's voice response system. In addition, a prescription can be "dropped-off" by a prescriber/doctor telephoning or faxing a customer's prescription to a pharmacy. Further, a prescription can be "dropped-off" via a drive-thru window.

The roles and responsibilities of the drop-off workstation(s) can dedicate persons staffing the drop-off workstation(s) to conducting data entry for all prescriptions "dropped-off" at a pharmacy regardless of the method by which the pharmacy receives the prescription with the exceptions of new telephone and fax prescriptions and refill telephone prescriptions. A registered pharmacist must receive new telephone and fax prescriptions, e.g., received from prescribers/doctors, in order to comply with state regulations and to write the prescription data. Thereafter, the written prescription data can be given to a person staffing a drop-off workstation to conduct data entry. A technician, customer support associate or other support staff manning a production workstation can receive a refill telephone prescription as data entry for a refill prescription typically is completed relatively quickly and without the occurrence of those issues or problems described above that can affect the prescription processing. In addition, when needed, and as work volume and time permit, persons staffing production or quality assurance workstations can help attend to receiving "dropped-off" prescriptions.

At stage 420, a prescription transaction is immediately initiated, or soon after the pharmacy's receipt of the prescription, when a staff person begins data entry and provides an initial estimated prescription pick-up time. The initial estimated pick-up time can be a customer requested pick-up time or a pharmacy designated pick-up time. For in-store "drop-offs", a staff person begins to conduct data entry and provides an initial estimated prescription pick-up time to a customer while the customer is present at a drop-off workstation. In the case of refill telephone prescription, a staff person can begin to conduct data entry and provide an initial estimated prescription pick-up time to a customer while the customer is on the telephone. In other instances where prescriptions are received at the pharmacy by voice mail or fax, a staff person initiates a prescription transaction by beginning to conduct data entry and entering into a pharmacy's processing system an initial estimated prescription pick-up time requested or identified in the voice mail message or fax. If a prescription pick-up time is not designated or requested, a staff person can enter, accept or select an initial default estimated prescription pick-up time that can be determined by a pharmacy and/or provided by the pharmacy's information processing system for those prescriptions that do not designate a prescription pick-up time. For instance, for those prescriptions received from prescribers/doctors via voice mail or fax often prescription pick-up times are not indicated; hence, the method 400 can enable a pharmacy to apply an initial default estimated prescription pick-up.

At data entry, prescription data and customer information are entered into a pharmacy's information processing system, which can include, but is not limited to, one or more computers operatively connected to a local area network (LAN) or other network wherein the network can access stored prescription data, customer information and other information to enable prescription fulfillment.

As noted, the roles and responsibilities of the drop-off and production workstations identify and describe the specific tasks that staff persons manning the workstations are to perform, and, in many cases, need to complete before a prescription transaction can proceed to further stages of processing. In one aspect of the system and method 400, the roles and responsibilities are posted, e.g., using workstation cards listing roles and responsibilities, at each of the drop-off or production workstations, e.g., proximate to one or more computers of the pharmacy's processing system or displayed by one or more computer monitors of the system, for staff persons to access and view. The roles and responsibilities for each workstation discussed herein will become more apparent as each workstation is described below in further detail.

As noted above, the staff person initiates the prescription transaction by performing data entry and providing an initial estimated prescription pick-up time 420, e.g., a customer requested pick-up time or a pharmacy designated pick up time. The method 400 according to the invention uses real-time prioritization to place prescriptions in a work queue, e.g., via a pharmacy's information processing system, with respect to the estimated prescription pick-up time. Thus, prescriptions proceed through processing based on time-stamping prioritization and are fulfilled in accordance with such priority. The method further prioritizes on a real-time basis those prescriptions that customers choose to wait while the pharmacy fulfills the prescriptions to give those prescriptions, e.g., designated "waiters", priority over other prescriptions, as will be described below in further detail.

In addition, data entry 420 further includes entering prescription data and customer information, such as the number of prescriptions in an order group, information provided by the prescription, e.g., drug name, amount, dose, etc., and the customer's name, address and one or more preferred telephone numbers by which the customer may be contacted.

At stage 430, the staff person continues to process the prescription transaction, e.g., while the customer is present at the drop-off workstation or is on the telephone with the staff person, by checking the pharmacy inventory to confirm whether stock is sufficient to fill the prescription. If stock is insufficient, the staff person checks a delivery schedule to determine when the pharmacy may receive a shipment of the prescribed drug, e.g., which is typically scheduled on a routine and periodic basis such that the staff person can easily predict when the pharmacy will have sufficient stock. In the event the inventory is insufficient to fill the prescription in full or is deplete of the prescribed drug, the staff person can offer the customer partial fulfillment of the prescription or a date by which the prescription can be filled in full, respectively. Despite whether the pharmacy has sufficient stock to meet the prescription requirements, the prescription transaction can then proceed to insurance adjudication.

At stage 440, the staff person continues to process the prescription transaction by performing insurance adjudication review, e.g., while the customer is present at the drop-off workstation or is on the telephone with the staff person. Insurance adjudication review confirms the customer's health insurance is active and whether such coverage will provide for the offered prescription. The staff person is to complete at least one prescription transaction through insurance review if a customer drops off a multiple of prescriptions for fulfillment. The defined roles and responsibilities of the drop-off workstations can identify a minimum number of prescriptions that the staff person can process for a single customer through insurance review at one time, e.g., 3 prescriptions or less, in order to avoid overwhelming the data entry stages.

When prescription data and customer insurance information are entered and/or confirmed, a prescription transaction is transmitted to a third party that conducts insurance adjudication review and provides the pharmacy with a confirmation or rejection of the prescription transaction. The staff person manning a drop-off workstation is responsible for initially attempting to resolve any insurance-related issues or problems that arise as a result of insurance adjudication review. In many cases, many minor problems can be resolved by the staff person while the customer is waiting at the drop-off workstation, or is on the telephone with the staff person, including, for example, correcting a policy number, entering a new policy number not previously entered, correcting the spelling of customer's name or correcting the customer's date of birth.

If an extended effort is required to resolve an insurance issue or problem, the staff person explains the problem to the customer while the customer is present at the drop-off workstation, or is on the telephone with the staff person, and asks for some time to resolve the issue or problem. For instance, many insurance issues or problems require the pharmacy to contact a third party, such as an insurance provider or a prescriber/doctor. In some cases, the customer's insurance coverage prevents refilling a prescription too soon, or requires prior authorization by an insurance provider or a prescriber/doctor to fill the prescription. If time permits, the staff person can proceed to contact the appropriate third party while remaining in communication with the customer. However, if the problem cannot be resolved without further effort, the staff person can indicate that the pharmacy will contact the customer when the problem has been resolved. At this point, the customer is aware of the problem and the staff person/pharmacy can reset the customer's expectations with respect to the prescription pick-up time.

At stage 450, with successful data entry, inventory stock check, refill authorization and insurance adjudication review, the staff person either can confirm the initial estimated prescription pick-up time determined at the outset of the transaction or can reset the estimated prescription pick-up time in view of any issue or problem that has arisen and has been or can be resolved. The confirmed or reset estimated prescription pick-up time is retained and/or entered into the pharmacy's processing system to thereby prioritize fulfillment of the prescription in a work queue based on the confirmed or reset estimated pick-up time. For instance, if a customer requests an initial estimated pick-up time, the staff person either confirms or resets the estimated pick-up time in response to the outcome of data entry activities including inventory check and insurance adjudication review. In the event of a successful outcome, the estimated pick-up time is retained in the pharmacy processing system, whereas if the outcome is not successful and requires some problem resolution, the estimated pick-up time can be reset in the pharmacy processing system to account for such resolution.

By confirming or resetting the estimated prescription pick-up time after the staff person has completed data entry, inventory stock check, refill authorization and insurance adjudication review, a realistic and relatively accurate estimated prescription pick-up time can be given to the customer and can be entered into the pharmacy's processing system because many issues or problems associated with the transaction would have been uncovered during data entry 420, inventory check 430 and/or insurance review 440 stages and, in many instances, while the pharmacy is in communication with the customer. In addition, the pharmacy and the customer can have knowledge of any issues or problems, as the staff person will have noted and conveyed such issues or problems to the customer at the drop-off 410, data entry 420, inventory check 430 and/or insurance review 440 stages of the process 400. The customer's expectations are thereby set according to whether data entry, inventory check and insurance review have been successful or unsuccessful. The confirmed or reset estimated pick-up time the staff person promises the customer can meet the customer's expectations, and can thereby enhance the customer's satisfaction with the pharmacy's services regardless of whether the initial data entry, inventory check and/or insurance review were successful. In addition, as will be described below in further detail, by uncovering problems with the transaction during early stages of processing and setting the customer's expectation of an estimated pick-up time with respect to whether resolution of any issues or problems is required, helps to avoid or prevent communication of any outstanding problems to the customer for the first time during the pick-up stages of processing when the customer least expects such problems.

At stage 460, after successful completion of data entry, inventory check, refill authorization and insurance adjudication review, the staff person can further prioritize fulfillment of the prescription by identifying the prescription as a "waiter", e.g., the customer will wait in the pharmacy store while the prescription is being fulfilled, or as a "non-waiter", e.g. the customer will return at a later time to pick up the fulfilled prescription. The staff person can ask the customer if they would like to wait for the prescription to be filled or would prefer to return to the pharmacy at a later time for pick-up.

In one aspect of the method 400 according to the invention, an initial estimated pick-up time provided at the outset of the transaction can be confirmed or reset for a "waiter" prescription transaction. An initial estimated pick-up time for a "waiter" can be confirmed or reset depending upon the number of prescription transactions, including "waiter" and "non-waiter" transactions, at various stages of processing as identified in any of a number of work queues. For instance, a staff person at a drop-off workstation can review an "all work queue" in the pharmacy processing system that lists all prescriptions at various stages of processing. In addition, the staff person can review a "production queue" that identifies a list of the prescription transactions currently in production stages to be filled or are being filled, and from which prescription labels and receipts are generated, e.g., printed, from the data entered into the pharmacy's processing system. The production queue sorts an overall picture or list of those prescription transactions in-line for production or at production stages by estimated pick-up times, e.g., confirmed or reset. The transactions are thereby time-stamped and the production queue prioritizes fulfillment of prescriptions by the estimated pick-up times.

The production queue can further prioritize fulfillment of prescription transaction by giving priority to "waiters" over all other transactions, and within those "waiter" transactions sorting such transactions by estimated pick-up times. Those transactions listed in the production queue as "waiters" can appear first or at the top of the production queue such that prescription labels and receipts for "waiters" will be generated/printed first or from the top of the production queue and thereby will be presented to production workstations first for fulfillment. The production queue can generate/print labels and receipts either at the drop-off workstation and/or at the production workstation. A certified or otherwise trained technician can dispense the prescriptions in the order with which the production queue generates/prints the prescription labels and receipts to thereby process and fulfill prescriptions according to the estimated pick-up times of the prescription transactions. In addition, the production queue can generate/print, e.g., automatically, a notice or a sticker, e.g., a colored sticker marked "waiter", with the prescription label or receipt to identify those transactions in the production queue that are "waiters".

Thus, the production queue can serve as a guideline or basis from which the staff person can confirm or reset an initial estimated prescription pick-up time, and, in the case of "waiter" transactions, can confirm or reset how long a customer will wait for his/her prescription to be filled. For instance, at the outset of a prescription transaction at which data entry begins, an initial estimated pick-up time can be provided to a customer for a "waiter" prescription and can be, for instance, for a time within 15 minutes of the transaction initiation. Depending on the outcome of data entry, inventory check, refill authorization and/or insurance adjudication review, the estimated pick-up time for the "waiter" can be confirmed or revised. In addition, the estimated pick-up time can be further confirmed or revised by a review of the all queue and/or the production queue that identifies the number of "waiter" and "non-waiter" transactions to be filled or are being filled. The customer's expectations are thereby initially set and then confirmed or reset with respect to the estimated pick-up time in view of the number of "waiter" and "non-waiter" transactions.

In another aspect of the method 400 according to the invention, the pharmacy processing system can be programmed to default to permitting entry of an estimated pick-up time for a "waiter" prescription only within a defined or programmed period of time, e.g., any time less than 30 minutes. In most cases, the staff person can likely confirm an estimated pick-up time for a "waiter" within the default period of time, if no issues or problems are uncovered during data entry. The staff person can be further provided with guidelines by which to base an estimated pick-up time that he/she can quote to the customer of a "waiter" prescription, depending upon the number of "waiter" prescriptions listed in the production queue. For instance, such guidelines can be identified in the roles and responsibilities workstation card posted at the drop-off workstation, or can be provided as one or more screens displayed by computer monitors of the pharmacy's processing system. For instance, guidelines can designate a maximum number of "waiters" in the production queue and/or in a quality assurance queue before the staff person can confirm or reset an estimated pick-up time for greater than 15 minutes for a "waiter" transaction. The quality assurance queue identifies those prescriptions that have been dispensed and are presently at a stage of quality assurance whereby a pharmacist reviews the prescriptions before the prescriptions proceed to a pick-up stage. For instance, the pharmacy processing system and/or the roles and responsibilities of the drop-off workstations can identify that if ten or more "waiter" prescriptions are currently in the quality assurance queue, then the staff person cannot confirm or reset an estimated pick-up time of less than 15 minutes. The staff person can then provide the customer with a reasonably accurate expectation of when the customer can pick-up the "waiter" prescription and can avoid promising a pick-up time and setting customer expectations that cannot be met.

Referring to FIG. 4A, in a further aspect of the method 400 according to the invention, a pharmacy's information processing system can be configured and/or programmed to produce, e.g., automatically, a modifiable guide by which a staff person can judge the estimated wait time for a number of "waiter" prescriptions. The guide is accomplished by determining the number of prescription transactions in the customer's order along with determining the number of prescription transactions that have estimated pick-up times due within a given period of time, e.g., within 15 or 30 minutes. The guide will give pharmacy staff an ability to relay a relatively accurate wait time to the customer and to organize their workflow more efficiently.

As shown in FIG. 4A, a guide can include the Estimated Wait Time Table 470 that the pharmacy's information processing system can generate, for instance, during data entry to provide a staff person with a tool by which to estimate a relatively accurate pick-up time for one or more newly entered "waiter" prescriptions. The Wait Time table 470 includes an X-axis 471 that identifies the number of prescriptions per customer, or per order, or per order group, and a Y-axis 472 that identifies the number of relevant prescriptions in one or more work queues. The relevant prescriptions can include "clean" waiter prescriptions, "clean" non-waiter prescriptions and emergency prescriptions wherein the term "clean" refers to those prescriptions that do not have any associated issue or problem related to, for instance, insurance adjudication review. A staff person can review the Table 470 and determine the estimated wait time for one or more "waiter" prescription transactions.

The wait times that are listed in the Table 470 can be automatically calculated by the pharmacy's processing system, or can be manually calculated by a staff person according to the following operations. The production queue and the quality assurance queue can be reviewed to determine a number of "clean" waiter prescriptions that have estimated pick-up times of not more than a given period of time, e.g., not more than 60 minutes. The production and quality assurance queues can be further reviewed to determine a number of "clean" non-waiter prescriptions that have estimated pick-up times of not more than a given period of time, e.g., 60 minutes. Using the values identified along the X- and the Y-axes 471 and 472 of the Table 470, an estimated wait time for a given number of newly entered waiter prescriptions for a customer, an order or an order group can be determined based on the number of newly entered waiter prescriptions and the number of "clean" waiter prescriptions in the production and quality assurance queues. This estimated wait time can be referred to as wait time A. Similarly, using the values identified along the X and Y axes 471 and 472 of the Table 470, an estimated wait time for the given number of newly entered waiter prescriptions can be further determined by based on the number of "clean" waiter prescriptions in the production and quality assurance queues plus some percentage, e.g., 50%, of a number of "clean" non-waiter prescriptions in the production and quality assurance queues. This estimated wait time can be referred to as wait time B. From a comparison of the wait time A to the wait time B, an estimated wait time a staff person can provide is determined. For instance, if wait time A is greater than 20 minutes, the estimated wait time for the one or more waiter prescriptions is the wait time A, as determined using the Table 470. If the wait time A is less than 20 minutes and the wait time B is greater than 20 minutes, the estimated wait time a staff person can provide is 20 minutes. If both the wait time A and B are less than 20 minutes, the estimated wait time a staff person can provide is the wait time B. If the estimated wait time is in excess of a determined and/or programmed time, e.g., 30 minutes, the pharmacy processing system can display a message that the estimated wait time exceed the determined/programmed time.

In addition, the system can further display, e.g., automatically, an estimated wait time for one or more newly entered waiter prescriptions when a number of the newly entered waiter prescriptions per customer, order or order group is entered. The system can further default to the estimated wait time for newly entered waiter prescriptions when a staff person enters an estimated pick-up time. If the calculated wait time, as determined by the processing system, is a determined and/or programmed time or less, e.g., 30 minutes or less, a staff person can center a code, e.g., a "W", with no time value for an estimated pick-up time. If the calculated wait time is greater than, e.g., 30 minutes, or the functionality generating the Estimated Wait Time Table 470 is not configured in the pharmacy processing system, the staff person can enter a value for an estimated pick-up time for newly entered waiter prescriptions. If the staff person enters a code, e.g., a "W", with no value of an estimated pick-up time, the system can use the calculated wait time to determine the estimated pick-up time.

At stage 470, when data entry, refill authorization, inventory check and/or insurance review are not successful, the staff person can inform the customer what the problem is and how the pharmacy will attempt to correct the situation while the customer is at the drop-off workstation, or is on the telephone with the staff person. The prescription transaction can be completed for a cash sale, for instance, in those situations in which the customer's health insurance will not provide coverage or requires prior authorization from an insurance provider or a prescriber/doctor. The customer, however, is aware of this problem at the data entry 420 and/or the insurance review 440 stages and does not learn of this problem for the first time at a later stage of processing, such as when the customer attempts to pick-up the prescription. When informed of the problem, the customer is thereby given the opportunity to agree to allow the transaction to proceed as a cash transaction.

As noted above, depending upon the issue or problem associated with the transaction, the staff person can indicate what efforts will be made to resolve the problem and the amount of time the pharmacy will need, e.g., from a few minutes to a few days, for resolution. The staff person can then either provide the customer with an estimated pick-up time in view of the problem to be resolved or can request the customer telephone the pharmacy before attempting to pick-up the prescription. For instance, if the customer's prescriber/doctor must be contacted, the staff person can indicate that this is required and can quote an estimated pick-up time, e.g., within 24 or 48 hours, or can ask that the customer telephone the pharmacy within a given time, e.g., within 24 or 38 hours, to check if the problem has been resolved. If an estimated pick-up time is quoted to the customer, the time and the date of quoted pick-up is entered into the system.

At stage 480, the staff member initiates resolution of the problem associated with the prescription transaction by entering information into an "action note" and designating the transaction in the pharmacy processing system as an "exception", which is listed in an "exception queue". The exception queue lists those prescription transactions that require resolution of one or more issues or problems related to data entry, inventory, refill authorization, insurance adjudication review and/or any other issue that affects processing. The exception queue can indicate whether the customer was provided with an estimated pick-up time and/or indicates information related to an issue or problem associated with the prescription transaction and the steps taken or need to be taken to resolve the issue or problem. In one aspect of the system and method 400, such prescription transactions can be similarly sorted by estimated pick-up times, if provided.

The staff person is the originator of the action note and must provide information in the note to meet certain objectives including, but not limited to, identifying the issue or problem to be resolved, identifying steps taken toward problem resolution, indicating the outcome of the steps taken and providing documentation of pharmacy efforts to contact the customer regarding problem resolution. Information that staff persons can provide in the action note can include, but are not limited to, whether a pharmacist must speak with the customer, the status of inventory, insurance rejection and reasons for rejection, whether "no-refill" status and date and time prescriber/doctor contacted, date and time of customer notification, e.g., informed customer at drop-off, spoke to customer on telephone, left customer voice mail message, and any notes concerning efforts to resolve a problem and the outcome of such efforts. The action note can be attached to the prescription label and/or receipt that the staff person generates/prints from the transaction information entered into the production queue of the pharmacy processing system. The action note thereby remains attached to the prescription label and/or receipt as it moves through the various stages of processing and can be completed at the drop-off or production workstations, as described below in further detail.

The action note provides pharmacy personnel with a uniform place and format to document any problem, all attempts to resolve a problem and any attempts both successful and unsuccessful to contact a customer to inform the customer of the progress of resolving the problem. In addition, the action note provides sufficient information related to resolution of any problem associated with a prescription transaction such that any member of the pharmacy staff can fully explain the problem to the customer or another member of the staff from the information appearing in the action note. In particular, the action note provides a staff person manning a pick-up workstation, as will be described below in further detail, with sufficient information to explain the problem to the customer when the customer returns to pick-up his/her prescription and to explain the efforts taken, or those efforts that need to be taken, to resolve the problem. The action note can be provided in a paper format to be completed manually by hand, or can be provided in an electronic format, e.g., as part of a data entry format of the pharmacy processing system. Once initiated, the action note is attached to a prescription label and/or receipt that are generated from the production queue. In an electronic format, the action note can be printed along with a prescription label and receipt and can be attached to such label or receipt for further processing.

In the event the problem is not resolved by the confirmed or reset estimated pick-up time, the staff person can contact the customer before the promised pick-up time to communicate to the customer that the problem has not yet been resolved. The roles and responsibilities dedicate the staff persons of the drop-off workstations to periodically checking the exception queue to resolve third party issues for all types of prescriptions, when time permits. Alternatively, the pharmacy can inform the customer that the problem has not been resolved when the customer contacts the pharmacy as requested. Communication with the customer upon discovery of the issue or problem, and thereafter to convey whether the issue or problem has been resolved, enables staff persons to set and reset the customer's expectations by providing a revised or new estimated pick-up time as a result of early identification and resolution of issues and problems.

In addition, as noted above, one or more staff persons at the drop-off workstations check the exception queue, when time permits, to review those transactions that require resolution of some issue or problem by contacting a third party, e.g., an insurance provider or a prescriber/doctor, and to thereby attempt to resolve issues and problems, as described above. If problems of those prescription transactions identified in the exception queue have not been or cannot be resolved, staff person at the drop-off workstations telephone customers to inform customers that the problems cannot be resolved before promised pick-up times or cannot be resolved. In addition, staff persons complete action notes for those prescriptions having unresolved issues and attach the action notes to the prescription labels and/or receipts.

At stage 490, upon completion of data entry and resolution of any resolvable issue or problem uncovered during stages of data entry 420, inventory check 430, refill authorization and/or insurance adjudication review 440, the prescription transaction proceeds into a work queue or, as disclosed above, the production queue and proceeds to a production workstation. The production workstation can be staffed by one or more registered pharmacists (RPh), certified or otherwise trained technicians (CT), and/or customer support associates (CSA), e.g., a support staff person, while in most instances CTs and CSAs dispense prescriptions. The transaction is generated/printed from the production queue as a prescription label and receipt and is generated/printed according to the time-stamping priority, as described above. In addition, the transaction is given further priority if it has been identified in the production queue as a "waiter". Either an RPh or a CT can review the printed prescription label and receipt, and dispense prescription medication into a container according to the prescription.

Like the staff persons at the drop-off workstations, the CTs that staff the production workstation have defined roles and responsibilities that are posted, e.g., using workstation cards disposed proximate to one or more computer monitors of the pharmacy processing system or displayed as one or more screens on one or more computer monitors of the system. The defined roles and responsibilities of the production workstation can include, but are not limited to, printing and filling prescriptions and printing and filling "waiter" prescriptions first, answering pharmacy telephone and directing call to appropriate person, and handling refill telephone prescriptions, e.g. verify refill authorization, pharmacy inventory stock, and accuracy of preferred customer contact telephone numbers on record, while in communication with the customer by telephone, as described above. For those "call-in" prescriptions that have insurance issues or problems, the production workstation does not conduct insurance adjudication review. While on the telephone with the customer, the CT at the production workstation can check inventory and can provide the customer with inventory status. If the medication is out-of-stock or only a partial prescription can be provided, the CT informs the customer while on the telephone and initiates an action note. Thereafter, the CT can complete the action note and can contact the customer when the full or partial prescription will be ready.

The CT can check the production queue as often as possible and can generate, e.g. print, the prescription transactions from the production queue. The roles and responsibilities can identify a maximum number of prescriptions that can be processed at one time, e.g., limited number of prescriptions in an order group, to manage workflow and to minimize/avoid prescription backlog. In addition, to provide an overlap of coverage at the drop-off workstations and pick-up workstations, production staff can assist at drop-off and pick-up as needed, if time and work volume permits, as CT can handle those tasks assigned to the drop-off and pick-up workstations.

After completing production, dispensing the prescription, the CT identifies whether the prescription is a "waiter" by affixing a colored sticker marked "waiter" to the prescription container and/or by calling out a "waiter" has been fulfilled, and thereafter transfers the fulfilled prescription to one or more appropriate storage or holding areas or bins, each appropriately labeled for "waiter" and "non-waiter" prescriptions.

At stage 492, the fulfilled prescription is taken from the storage or holding area or bin and passes to a quality assurance or prescription verification workstation whereby an RPh conducts a verification of the fulfilled prescription that incorporates a DUR review, with "waiter" prescriptions being verified and reviewed first. If the fulfilled prescription passes the DUR review, the prescription is then transferred to one of two pick-up workstations. If the prescription does not pass the DUR review, the RPh can attempt to resolve any issue or problem, for instance, by telephoning the prescriber/doctor and/or the customer. In this case, the RPH resolves the problem and/or notifies the customer of the problem in advance of the estimated customer pick-up time. After completion of the verification process, the RPh calls out that a "waiter" prescription has completed quality assurance and is to pass to a pick-up workstation.

The method 400 according to the invention positions the DUR review such that it is performed well after the prescription transaction has been initiated and data entry completed, as well as after resolution of any issue or problem associated with the transaction and entry of the transaction into the work queues. An RPh can thereby remain engaged in his/her primary responsibilities of production and quality assurance.

Additional roles and responsibilities of the quality assurance workstation can include, but are not limited to, verifying that action notes are fully complete and returning to originator for further information, if needed, checking periodically prescriber/doctor voicemail and managing overall workstation activities and workflow.

At stage 494, once the DUR review is completed, the fulfilled prescription proceeds to one or more pick-up workstations and is stored in appropriately labeled storage areas or bins. A staff person similarly must follow defined roles and responsibilities such as, although not limited to, calling out last name of customers of "waiter" prescriptions, greet customers, ask customer for number of prescriptions they are picking up, verify customer address before cashiering sale, communicating any action note details to customer and making offer to counsel according to state regulations. In addition, if three or more customers are in line for pick-up, the staff person is required to request assistance from other pharmacy staff. In the event of an unresolved issue or problem, the staff person does not leave the pick-up workstations, but passes the prescription to a designated person to handle at the drop-off workstations or the production workstation.

To further enhance communication between pharmacy personnel and customers, guidelines for customer contact can be provided for various situations. Such guidelines can include recommended conversational scripts that pharmacy personnel can use for communication with customers to help to convey information to customers and to request information from customers. Such guidelines can address such situations as, but are not limited to, obtaining required insurance information required, informing customer prescription being refilled too soon, informing customer prior authorization from insurance provider is required, and informing customer inventory is out-of-stock or can provide partial prescription. Such guidelines can be readily available at all workstations.

Figure 5:
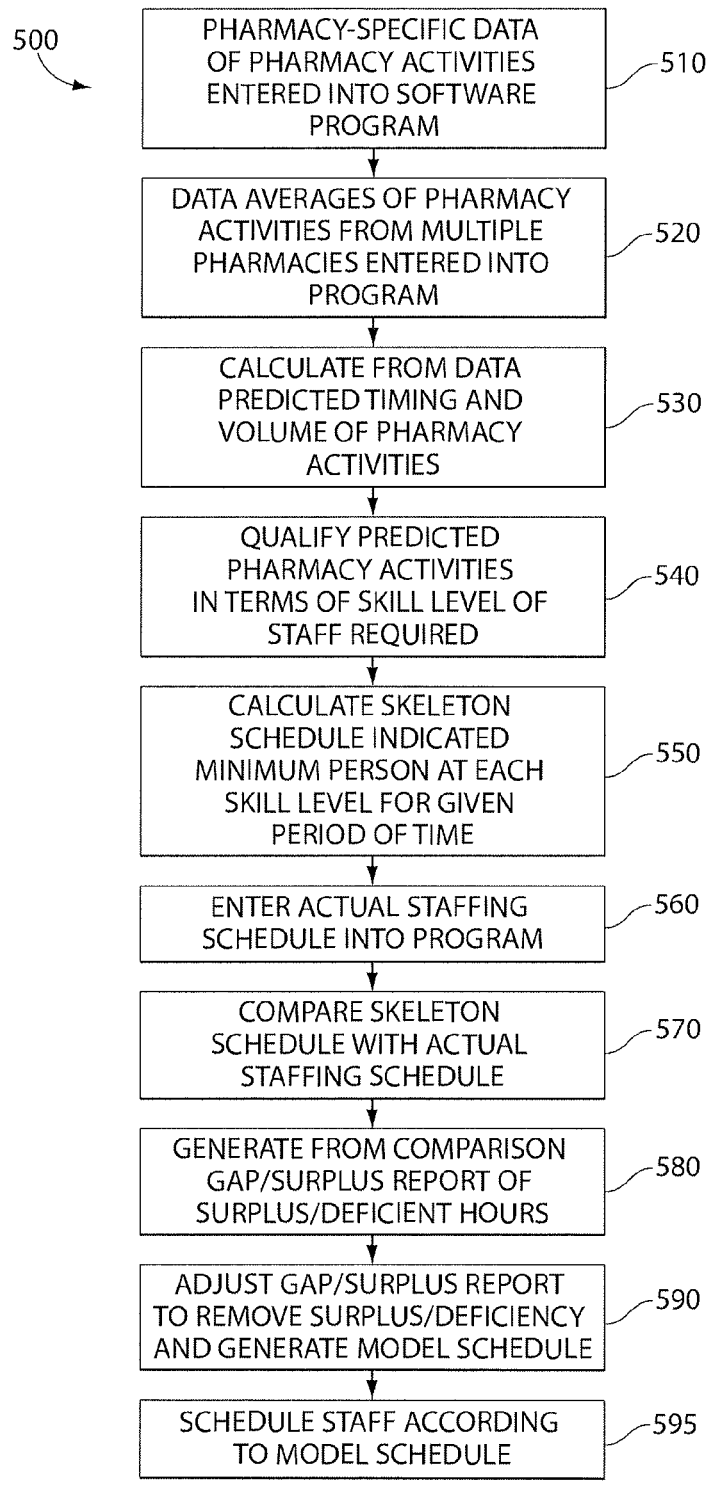
FIG. 5 is a flow diagram of stages of a method of scheduling staff according to the invention.

Referring to FIG. 5, the invention further provides a method 500 for determining and implementing a staffing schedule for a pharmacy that helps to provide optimal staffing coverage for various pharmacy activities. The scheduling method 500 according to the invention is disclosed below in the context of providing pharmacy services, namely fulfilling and dispensing drug prescriptions, and is particularly suited for scheduling/staffing a stage-by-stage or compartmentalized workflow or process, such as that described above with respect to processing drug prescriptions, whereby various stages of the workflow/process require different skill levels. The scheduling method 500 helps a pharmacy to predict the number of staff that will be required for each skill level for a given day and for specific hours of the day and to create from such predictions staffing schedules that help to meet and optimize a predicted workflow. The method 500 uses store-specific data and chainwide data from a multiple of stores that are tracked during pharmacy operation to determine staffing needs. In particular, the method 500 of the invention uses store-specific and/or chainwide data that accounts for and helps to predict staffing needs required to recognize and to resolve issues and problems associated with drug prescription fulfillment at early stages of processing. The method 500 according to the invention essentially determines and implements a staffing schedule that places the right number of people with the right skill level at the right place at the right time of day to thereby help to optimize pharmacy services. Those of ordinary skill in the art will appreciate that the scheduling method 500 according to the invention is not limited in application to pharmacy services and can be applied in other scheduling contexts that require staff scheduling according to different skill levels as required at various stages of workflow or a process, such as scheduling staff to provide other types of services, including retail or financial services.

The staff scheduling method 500 according to the invention can be implemented in a variety of ways including through a software program configured for operation on one or more computers of a single pharmacy store and/or a multiple of stores, e.g., that are operatively connected via a local area network (LAN) and/or other type of data communications network, such as the Internet, and further configured for storage on a computer readable memory. A software program can be established for controlling pharmacy computers to collect and to store various store-specific data and/or chainwide data from which the timing/occurrence and the volume of key pharmacy activities can be predicted. For instance, store-specific data and chainwide data can be used to predict the timing of a pharmacy activity in terms of specific hours of a business day and specific days of the week, and to further predict the volume of such activity during these times. The software program can be further coded to convert the predicted pharmacy activities into estimated numbers of total staff required and staff required at each skill level, e.g., registered pharmacist, certified or otherwise trained technician, customer support associate, or support staff, for specific hours of a business day and specific days of the week to carry out the predicted pharmacy activities. The software program can instruct the pharmacy computers to calculate a recommended "skeleton" staffing schedule for a period of time, e.g., one week, two weeks or a month, from the estimated numbers of staff required. The skeleton staffing schedule recommends the number of staff at each skill level, e.g., the number of pharmacists, technicians or support staff, to be scheduled for each hour and each day based upon the predicted pharmacy activities and the estimated numbers of staff required at each skill level. The program can also instruct the pharmacy computers to compare the skeleton staffing schedule for a period of time, e.g., one week, to an existing staffing schedule for a similar period of time, e.g., a prior week. The software program can further cause the pharmacy computers to generate from the comparison of the skeleton and existing schedules, a gap/surplus report that summarizes the staffing surpluses and deficiencies for each hour of each day to be scheduled. The software program can be coded to enable a user or scheduler to adjust a staffing schedule by removing or minimizing surpluses and/or deficiencies identified in the gap/surplus report to meet the recommended staffing for each hour, and to produce a model staffing schedule from the adjusted gap/surplus report from which staff are scheduled. In addition, the software program can be further coded to automatically track, e.g., record and store, pharmacy-specific information and to receive/download regional chainwide data files for use as data inputs in producing staffing schedules. Further, the software program can instruct the one or more computers to record, store and/or provide any data, files or other relevant indicia associated with providing pharmacy services that can be used to help to calculate staffing schedules.

In addition, a computer readable memory, e.g., random access memory (RAM), read only memory (ROM), volatile memory and/or magnetic, electro optical and/or one or more other storage memory devices, can store the software program described above for implementing and managing the staffing method 500 according to the invention. The computer readable memory can be incorporated with one or more computing devices including, for instance, a mainframe computer, a personal computer, a laptop computer, an Internet appliance, a workstation, an interconnected group of computers and/or any other device(s) configured to help to implement and manage the system and method 300 described herein.

As noted, the scheduling method 500 according to the invention will be described herein in the context of providing pharmacy services, and as implemented through a software program, as described above, stored in a readable memory and operating on one or more pharmacy computers operatively connected through a LAN and/or other data communications network. As shown in FIG. 5, the method 500 is exemplary only and is not limiting, and can be altered or modified, e.g., by adding, deleting and/or rearranging stages.

At stage 510, actual store (pharmacy)-specific data is entered into the scheduling software program, as described above. The pharmacy-specific data can be tracked, e.g., recorded and stored, by the software program, and can include, but are not limited to, a number of register transactions per hour, a number of new prescriptions dispensed per hour, a number of refill prescriptions dispensed per hour, a percentage of new to refill prescriptions, an estimated or actual number of telephone calls per hour, a percentage of prescriptions "called-in" via a pharmacy's voice response system (voice mail), hours the pharmacy is open for business, whether the pharmacy has a drive-thru window, a maximum legal ratio of registered pharmacists to technicians required according to state law, anticipated dates and times of warehouse inventory delivery, and a predicted weekly prescription volume.

Figure 6:
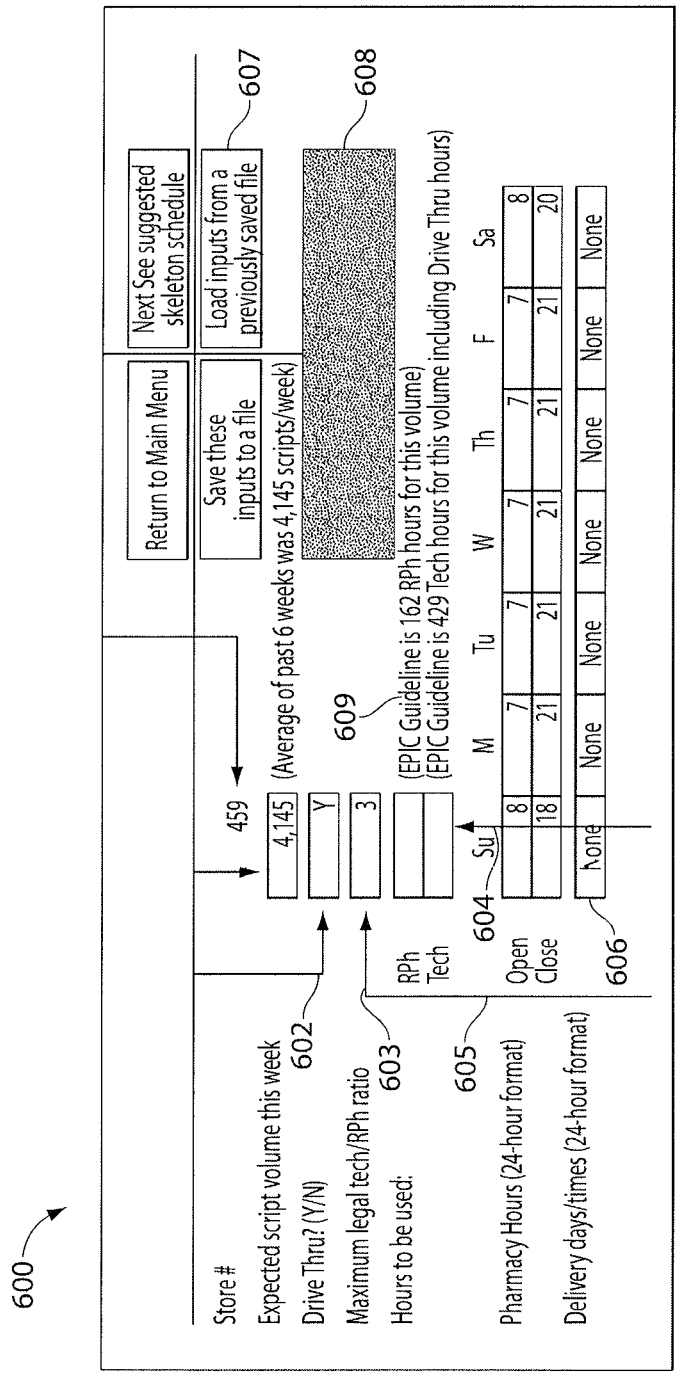
FIG. 6 is a schematic diagram of a data entry screen for initiating one or more stages of the method shown in FIG. 5.

Referring to FIG. 6, and with further reference to FIG. 5, in one aspect, the method 500 according to the invention provides one or more data entry screens 600 that can be produced by the software program and displayed on one or more monitors of the pharmacy computers for entry of pharmacy-specific data. A data entry screen 600 can be accessed to initiate generation of a staffing schedule for a designated period of time, e.g., one week, two weeks or a month. A user or scheduler enters pharmacy-specific data into the data entry screen 600 by populating data fields including predicted weekly prescriptions for the forthcoming month 601, an indication of whether the pharmacy has a drive-thru, e.g. yes/no 602, a maximum legal ratio of pharmacists to technicians 603, a number of hours to be allocated for pharmacists and for technicians 604, the pharmacy's hours of operation 605, days and times of anticipated inventory deliveries 606, and other pharmacy-specific data inputs that can be accessed from stored data or data files 607.

If the data field for the predicted weekly prescription volume for the forthcoming month 601 is left blank, the program can be configured to default to an average weekly prescription volume of a defined period of time, e.g., the prior six (6) weeks, of the pharmacy's operation.

The number of hours a user or scheduler can allocate for pharmacists and technicians 604 can be determined with help from guidelines the pharmacy provides for a specific number of pharmacist hours and a specific number of technician hours to be allocated for a given predicted weekly prescription volume 601. As shown in FIG. 6, such guidelines 609 can be displayed in the data entry screen 600 in response to entry of a weekly prescription volume in the data field 601. The guidelines 609 can include either recommended numbers of pharmacist and technician hours to be scheduled or budgeted numbers of hours that a schedule should not exceed for a given period of time. A scheduler can thereby view the guidelines for recommended or budgeted hours and can enter in the data field 604 the numbers of pharmacist and technician hours to be scheduled.

In one aspect of the method 500 of the invention, the software program provides flexibility with respect to the hours allocated for certified or trained technicians and enables a scheduler to allocate as many technician hours as the scheduler desires or requires. The program is configured to use technician hours to adjust staffing surpluses and deficiencies, as will be described below in further detail, and to produce a staffing schedule that accommodates the predicted pharmacy activities. Technician hours rather than pharmacist hours are used to adjust staffing surpluses and deficiencies because pharmacist hours are typically allocated such that pharmacists have the same or consistent work schedule from week to week and/or from month to month.

The software program can define a default time format, e.g., a 24-hour format, to populate the data fields of the pharmacy's hours of operation 605 and the days and times of anticipated inventory deliveries 606. The scheduler can ensure the hours of operation 605 and the days and times of inventory delivery are correct 606, and can make appropriate adjustments by changing or removing data from the data fields 605 and 606, as these data inputs will affect how the program allocates pharmacist and technician hours for each day. Other pharmacy-specific data inputs can be accessed from stored data or data files 607 and can include data averages tracked from the pharmacy's activities during a specific period of time, such as, for instance, from the prior six (6) weeks, of the pharmacy's operation.

At stage 520, once the input fields of the data entry screen 600 are populated, chainwide pharmacy data 608 can be entered, e.g., by downloading one or more data files from the network. Chainwide data can include data averages estimated from a multiple of pharmacies, e.g., within a specific geographical region. Chainwide data can include, but are not limited to, the timing of incoming telephone calls, the timing of voice response system "call-ins", the amount of time certain activities take, e.g., date entry, production, quality assurance, outgoing telephone calls, or cashiering transactions, rates of insurance problems, rates of refill authorization problems and frequency of customer consultation. In particular, chainwide data can help to account for staffing needs in terms of the number of staff required at each skill level and the number of man-hours required for recognition and resolution of any problems that can arise during the early stages of prescription processing, such as, as described above, prescription drop-off 110 and data entry 120 stages of prior art methods. Chainwide data can be periodically downloaded, e.g., once a month, in order for the pharmacy store's program to include the latest or most current chainwide data.

At stage 530, once chainwide data is entered, the volume and the timing of pharmacy activities can be predicted from the pharmacy-specific and chainwide data for a specific period of time, e.g., one week, two weeks or a month. Pharmacy activities that can be predicted with respect to volume and timing according to the method 500 of the invention include, but are not limited to, data entry activities, such as prescription drop-off, prescription data intake, insurance adjudication review and contacting customers concerning problem resolution, as described above; production and quality assurance activities, such as dispensing drugs according to prescriptions, DUR review and customer consultation; cashiering activities; activities to handle incoming and outgoing telephone calls and faxes, e.g., to and from prescriber/doctor offices or insurance carrier offices; warehouse inventory delivery activities, meal breaks; and other downtime activities.

The chainwide data generally provide average times for certain pharmacy activities and can serve as relative predictors of how much time each pharmacy function or activity will take. The chainwide data predictors are related to the store-specific volumes of the pharmacy activities, e.g., corresponding pharmacy activities, and then scaled to determine the total number of hours required for the pharmacy activities. The timing of each pharmacy activity and its volume thereby can be predicted in terms of a number or volume per hour of each day and per day of each week, such that each hour of operation of a pharmacy's business day is predicted with respect to a particular pharmacy activity. For example, the number of prescriptions dropped-off for data intake can be predicted for each hour and for each day of the time period to be scheduled.

At stage 540, once the timing and the volume pharmacy activities are predicted, the activities are quantified and the total number of hours predicted. The activities are further qualified or divided by requisite skill level, e.g., pharmacist, technician or support staff, to generate a recommended minimum number of persons required at each skill level and a recommended total number of persons required to be scheduled for a period of time including a specific hour of a day and a specific day of the week, in order to handle the pharmacy workload for that time period.

The program essentially converts a predicted activity into a minimum number of personnel to complete the activity in terms of the activity's requisite skill level. For instance, predicted activities include activities that can be handled only by a pharmacist, activities that can be handled either by a pharmacist, or certified or otherwise trained technician, and activities that can be handled by any staff person, including support staff. The program is configured to recognize those activities that can be handled by either a pharmacist or a technician, and those activities that can be handled by any staff person. For example, for the pharmacist-only activity of quality assurance, the method can predict a minimum number of pharmacists that will be required for each hour of a day and for each day of a week based upon the predicted timing and volume of pharmacist activities, including drug dispensing, customer consultation, incoming doctor calls (according to most state laws/regulations) and based upon the legal ratio of pharmacists to technicians required. The predicted minimum number of pharmacists serves as a recommendation to the scheduler for creating a daily and a weekly staffing schedule. As another example, for activities requiring either a pharmacist or technician, such as production, the method predicts a minimum number of pharmacists plus technicians required for each hour of a day and for each day of a week. As a further example, activities that can be completed by any staff person, e.g., cashiering, would be similarly predicted as a minimum number of total staff required for each hour.

Figure 7:
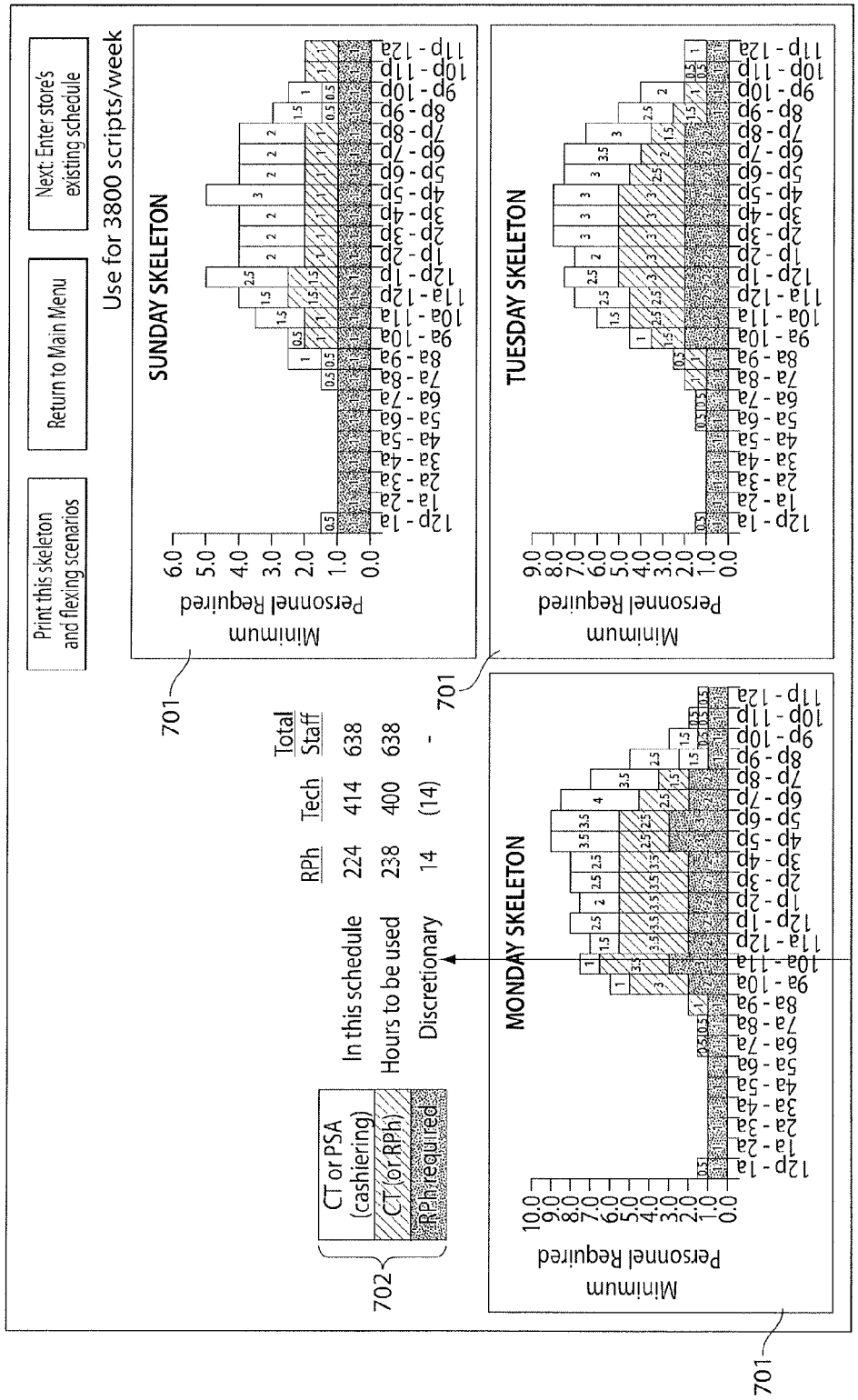
FIG. 7 is a schematic diagram of a recommended skeleton staffing schedule according to the method shown in FIG. 5.

At stage 550, once the recommended minimum number of pharmacists and technicians and the recommended total staff are determined, the software program produces a recommended "skeleton" staffing schedule that represents the minimum number of pharmacists, technicians and support staff required hourly and daily for the time period to be scheduled. Referring to FIG. 7, and with further reference to FIG. 5, the software program generates and displays at one or more of the pharmacy computers a recommended skeleton schedule 700. In one aspect of the method 500 according to the invention, the schedule 700 can be configured as a graphical representation of the minimum number of staff recommended for each day of a week and each hour of a day. As shown in FIG. 7, the schedule 700 can include a bar graph 701 for each day of a week to be scheduled and each bar graph 701 can display minimum staffing requirements for each hour of that day. The bar graph 701 can include an X-axis to identify each hour of the pharmacy's operation and a Y-axis to identify a recommended total number of staff persons. As shown in FIG. 7, each bar graph 701 can further illustrate a recommended minimum number of staff at each skill level for each hour such that the scheduler can determine how many pharmacists, technicians or support staff is recommended for a particular hour of a particular day. Each skill level can be identified or represented in the bar graph 701 by different colors and/or designs.

The schedule 700 can further display as a table, chart or other configuration 702, the number of pharmacists, technicians, customer support associates and the total staff hours the scheduler entered at the data entry screen 600 at the data field to allocate technician and pharmacist hours 604. As shown in FIG. 7, the hours the scheduler entered can be identified as "hours to be used" and serve as hours budgeted and within which the total hours schedule must fall.

In addition, the schedule 700 can display the number of pharmacist, technician and total staff hours that the software program has recommended hours for a particular period of time, e.g., a week or a month, as noted above. The recommended hours can be identified in the schedule 700 as "in this schedule". The software program can be configured to retrieve and to display in the skeleton schedule 700 the number of recommended pharmacist and technician hours. The recommended pharmacist and technician hours are calculated by the program and retrieved in response to the predicted weekly prescription volume 601 entered at the data entry screen 600. Recommended hours serve as a guideline for the scheduler and indicate the total number of pharmacist, technician and/or customer support associate or other support staff hours an actual schedule should include.

As shown in FIG. 7, often the budgeted pharmacist hours that the scheduler enters at the data entry screen 600 are in excess of the recommended hours in order to provide flexibility in pharmacist schedules. Extra pharmacist hours are designated "discretionary" for the scheduler to use as needed in scheduling staff. For example, pharmacist discretionary hours can be used to replace technician hours in order to provide a consistent work schedule for pharmacists and/or to reduce the number of technician hours and to thereby remain within the total number of budgeted hours. Because pharmacists can perform all technician-activities, discretionary pharmacist hours can replace technician hours without affecting performance of pharmacy activities.

Figure 8:
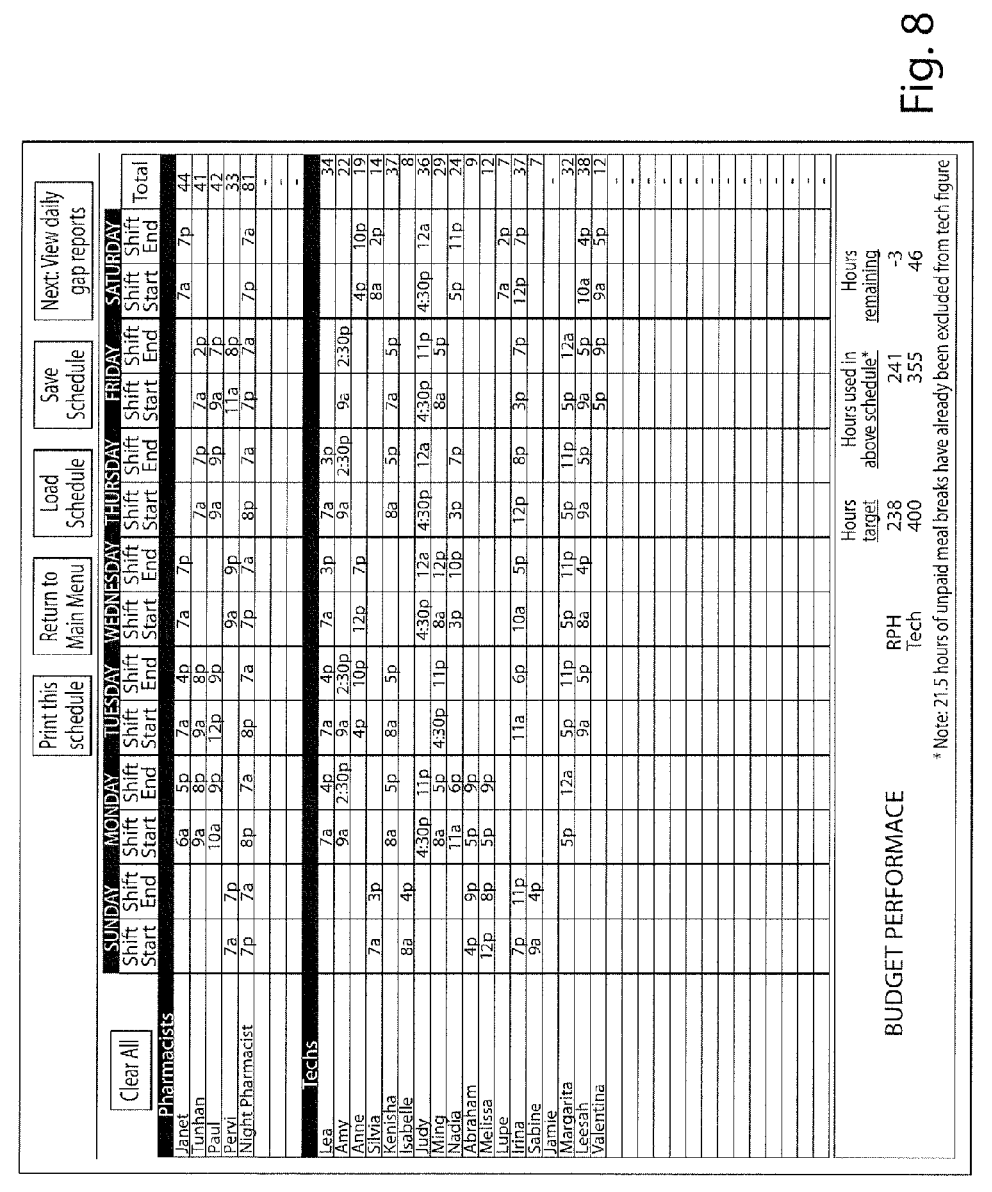

At stage 560, referring to FIG. 8 and with further reference to FIG. 5, a pharmacy's existing schedule can be entered or downloaded into one or more of the computers and can include existing pharmacist and technician schedules from a previous period of time, such as a previous week or month, that include total numbers of pharmacist, technician and support staff hours scheduled. Using the data of the previous work schedule enables the software program to compare the proposed schedule with a previous schedule to identify scheduling gaps and to direct the scheduler to changes that are required while minimizing employee availability conflicts, as described below.

At stage 570, the software program compares the recommended "skeleton" schedule 700 for a given period of time, e.g., one week, with the pharmacy's prior existing schedule for a similar period of time, e.g., a previous week, and generates from the comparison of the schedules a gap/surplus report. The gap/surplus report indicates any discrepancies between the recommended and existing schedules in terms of extra hours or shortage of hours for each hour of specific days of a week, e.g., Sunday, Monday, Tuesday, etcetera. In addition, the gap/surplus report can indicate the minimum number of total staff required for each hour of the day, and the number of RPhs and CTs to be scheduled.

Figure 9:
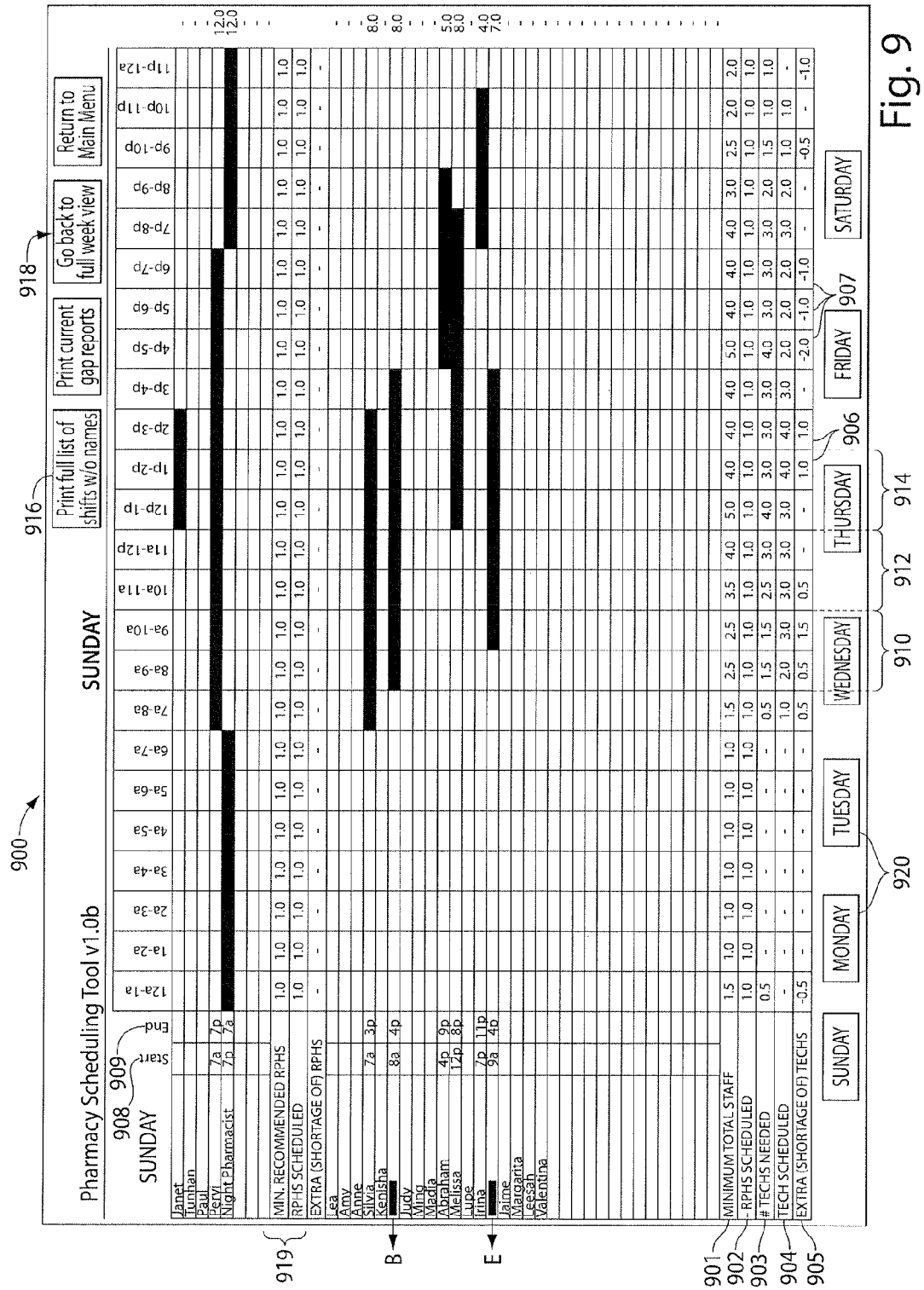
FIG. 9 is a schematic diagram of a gap/surplus report according to the method shown in FIG. 5.

Referring to FIG. 9, a gap/surplus report 700 for a single day, e.g., Sunday, is illustrated. In one embodiment, the software program can provide and display the gap/surplus report 900 as a graphical daily schedule that can be configured as a user interface to permit the scheduler to make adjustments to the schedule, as described below. Each day of a week can be displayed, and within each displayed day each hour of pharmacy operation can be displayed. Each day can include data fields identifying the minimum total number of staff scheduled for each hour 901, a minimum number of pharmacists scheduled for each hour 918, a number of pharmacists scheduled for each hour 902, a number of technicians needed for each hour 903, a number of technicians scheduled for each hour 904 and a discrepancy of hours between technician hours needed and scheduled 705 that is expressed in terms of a number of extra or shortage of technician hours for each hour. The software program calculates and identifies the discrepancy between hours scheduled and hours needed in terms of technicians hours because technician hours can be increased, decreased and shifted throughout the daily schedule without disrupting pharmacist schedules and to meet the skill level requirements identified for a specific hour of the day. The technician schedules can thereby be varied from day to day and from week to week, depending on the minimum recommended number of total staff to be scheduled per hour and the skill level required at each hour to handle the predicted pharmacy activities that occur during that hour. Thus, the software program essentially schedules technician hours according to the predicted timing and volume of pharmacy activities during a given hour of a given day in order to maintain consistent schedules for pharmacists.

As shown in FIG. 9, a significant surplus of technician hours is shown by cells numbered 906 and a significant shortage of technician hours is shown by cells numbered 907. The gap/surplus report 900 can be used to adjust the number of scheduled technician hours by removing or minimizing the discrepancies 905 between the technician hours needed 903 and the technician hours scheduled 904. In addition, cells can indicate a surplus or shortage of hours in terms of 0.5 hours, which are left to the discretion of the scheduler to treat as either zero hours or 1 hour.

In one aspect of the method 500 according to the invention, the discrepancies 905 can be removed or minimized by adjusting the "start" time 708 and the "end" time 709 of a work shift of one or more technicians. The software program can produce the gap/surplus report 900 with "start" and "end" columns 708 and 709, as shown, to display the beginning and end of each person's shift, e.g., based on a prior shift. The software program can further configured the "start" and "end" columns such that the "start" and "end" columns include data fields that the scheduler can access, e.g., via clicking a cursor on each column or the word "start" or "end", to change a time a technician shift starts and a time the technician shift ends to thereby alter or adjust the technician shift for a given day. For example, as shown in FIG. 9, during the hour from 4:00 p.m. to 5:00 p.m., a shortage of 2.0 technician hours has been determined and is displayed in the cell 907 as "−2.0" technician hours. To minimize or remove the two-hour shortage, the start and end times 708 and 709 of the shift, for instance, for technician "B" (8:00 a.m. to 4:00 p.m.) and for technician "E" (9:00 a.m. to 4:00 p.m.) can be adjusted such that each technician begins and ends his/her shift one hour later. Technician B's shift would cover the hours from 9:00 a.m. to 5:00 p.m. and technician E's shift would cover the hours from 10:00 a.m. to 5:00 p.m., such that technicians B and E overlap between 4:00 p.m. and 5:00 p.m. to thereby remove the two-hour shortage that the gap/surplus report identified between 4:00 p.m. to 5:00 p.m.

The gap/surplus report thereby allows the scheduler to adjust a daily, weekly or monthly schedule by the hour to ensure that during each hour the pharmacy is operating, the minimum total number of staff required are scheduled and the minimum number of staff required at each skill level are scheduled. In addition, the gap/surplus report enables the scheduler to review a weekly schedule in addition to the individual daily schedules by accessing the weekly schedule at 918 to view the weekly schedule to ensure that daily hours scheduled fall within the recommended or budgeted hours for a week.

At stage 590, a model schedule can be produced from the gap/surplus weekly and daily reports by adjusting hourly surpluses and deficiencies, as noted above, to provide a recommended model schedule that identifies the number of persons required at each skill level and the work shifts of each person, e.g., indicated as times that shifts begin and end. Actual scheduling of one or more persons to specific shifts can be accomplished using the model schedule. In addition, the software program can permit the model schedule to be generated, e.g., printed, without listing the names of pharmacists, technicians and/or support staff 916. In this way, the model schedule identifies when persons of specific skill levels are required and enables the scheduler to schedule certain shifts when they are needed rather than when persons desire to work and/or are available to work. The model schedule thereby helps to provide discipline with respect to scheduling staff.

At stage 595, the scheduler can use the model schedule to assign staff of each skill level to specific workstations at specific hours of the day and during specific days of the week. As shown in FIG. 9, the model schedule will indicate, for instance, that on Sunday between the hours of 8:00 to 10:00 a.m., the program has determined that one pharmacist and two technicians are required for a minimum total staff of three persons. As shown in FIG. 9, the minimum total staff for the hours of 8:00 to 10:00 a.m. 910, is indicated by the numeral 2.5, which can be interpreted at the discretion of the scheduler as either 2 persons or 3 persons.

Figure 10:
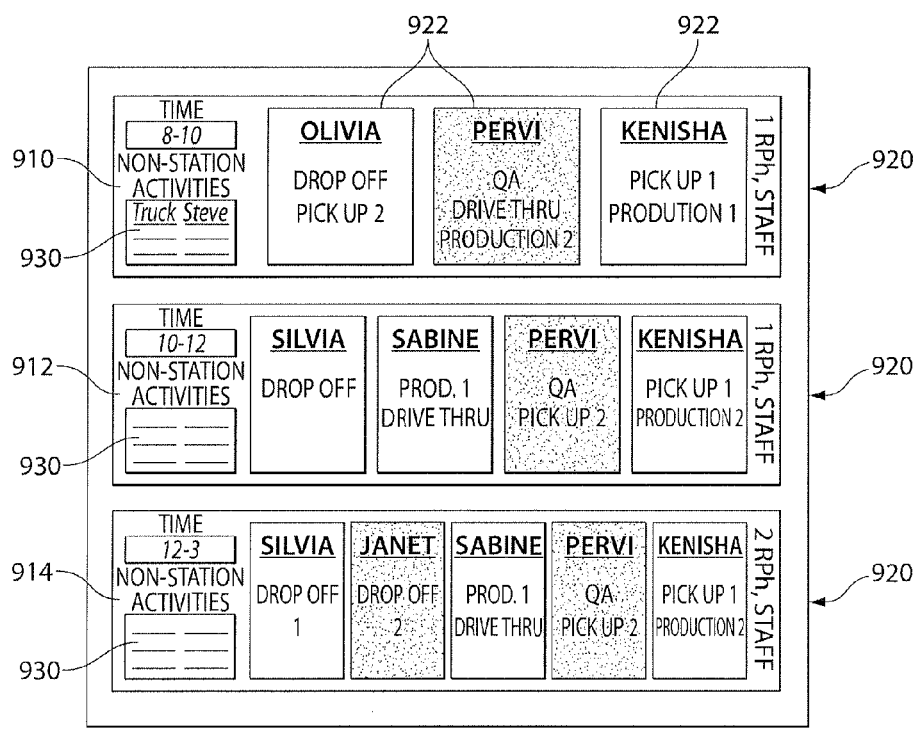
FIG. 10 is a schematic diagram of a workstation assignment board according to the method shown in FIG. 5.

Referring to FIG. 10, a sample assignment board is illustrated that can be used to assign persons according to skill level to one or more workstations. The assignment board can be configured to indicate specific periods of time 910, 912, and 914 that are scheduled, e.g., from 8:00 to 10:00 a.m., 10:00 to 12 noon or 12 noon to 3:00 p.m., the minimum number of RPhs and corresponding staff persons scheduled for each time period 920, and the name of the person scheduled and his/her workstation assignment(s) 922. The assignment board can be posted in an area of the pharmacy such that staff persons can know which workstation they are assigned to during specific hours of the day. For example, the 3 persons scheduled to work on Sunday between 8:00 and 10:00 a.m. 910 can thereby be assigned to one or more workstations dedicated for drop-off, production, quality assurance and pick-up. During other time periods, such as between 10:00 a.m. and 12 noon 912 and 12 noon and 3:00 p.m., additional staff can be added and/or workstation assignments can be added or changed to ensure sufficient staff having the requisite skill levels staff each workstation in response to the timing and volume of pharmacy activities. As shown in FIG. 10, workstations can be designated, for instance, as "Drop-Off 1" and "Drop-Off 2" or as "Production 1" and "Production 2" to identify each workstation. Each pharmacist and each technician can thereby be assigned to more than one workstation to help each workstation meet its tasks and to provide an overlap of staff when needed. A primary assignment can be highlighted, e.g., bold and/or larger text, in the assignment board to indicate a staff person's primary responsibilities or primary workstation assignment from secondary responsibilities or a secondary workstation assignment, such as helping at an additional workstation when needed and time permits. The assignment board can also help the scheduler to assign a particular workstation as a primary assignment to those persons with the strongest skills to handle the tasks of that particular workstation, which can help to optimize processing and enhance customer service.

Designated primary assignments also helps to ensure staff manning a particular workstation are dedicated or limited to a single type of pharmacy-customer interface, such as a staff person at one of the drop-off workstations is limited to interfacing with customers who enter the pharmacy store to drop-off a prescription at the drop-off workstation. By dedicating or limiting staff to a pharmacy-customer interface helps to promote and ensure optimal customer communication and service.

In addition, the assignment board can be used to assign additional task for specific individuals during specific times of the day as provided by a section 930 adjacent each time period 910, 912 and 914.

Having thus described at least one illustrative embodiment of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A non-transitory computer readable memory having a computer program configured for execution by a computer system to implement a method of controlling processing a drug prescription transaction in a pharmacy, the computer program comprising program instructions for:

recording in the computer system an initial estimated pick up time by which the drug prescription transaction will be fulfilled and available to a customer after receipt of the drug prescription transaction by the pharmacy, wherein the prescription transaction includes one or more prescriptions;

entering prescription transaction data into at least one work queue stored in the computer system to position the prescription transaction into the work queue, the work queue including data related to a plurality of other prescription transactions for fulfillment including a pick up time for each transaction;

prioritizing in real time a position of the prescription transaction in the work queue relative to the initial estimated pick up time or a computed reset estimated pick up time, wherein computing the reset estimated pick up time is in response to receiving data related to at least one of: (i) drug inventory for fulfillment of the one or more prescriptions, (ii) a third party insurance adjudication review or the refill authorization of the prescription transaction, and (iii) a number of prescription transactions in the work queue; and recording the reset estimated pick up time, when computed, in the computer system.

2. The computer program of claim 1 wherein computing the reset estimated pick up time of the drug prescription transaction includes resetting the initial estimated pick up time based on an outcome of at least one of: (i) checking the pharmacy drug inventory and (ii) obtaining insurance adjudication review or refill authorization, and further comprising prioritizing in real time the position of the prescription transaction in the work queue in accordance with the reset estimated pick up time.

3. The computer program of claim 1 wherein computing the reset estimated pick up time of the drug prescription transaction includes resetting the initial estimated pick up time to accommodate an estimated time to resolve at least one of: (i) insufficient pharmacy inventory for fulfillment of the one or more prescriptions in the prescription transaction and (ii) problems associated with the insurance adjudication review or the refill authorization, and further comprising prioritizing in real time the position of the prescription transaction in the work queue in accordance with the reset estimated pick up time.

4. The computer program of claim 1 further comprising entering data related to at least one of: (i) insufficient inventory for fulfillment of one or more prescription transactions and (ii) problems associated with the insurance adjudication review or the refill authorization, into at least one of: (i) the computer system and (ii) an action note configured to initiate resolution of at least one of the aforementioned.

5. The computer program of claim 1 comprising instructions for:

prioritizing in real time a position of the prescription transaction in the work queue by identifying the transaction as a waiter prescription transaction and placing the waiter prescription transaction in the work queue in a priority position for fulfillment relative to at least the positions of the plurality of other prescription transactions in the work queue, wherein the waiter prescription transaction includes one or more prescriptions being processed for fulfillment while a customer waits for processing and fulfillment of such waiter prescription transaction.

6. The computer program of claim 5 comprising instructions for:

prioritizing in real time a position of the waiter prescription transaction in the work queue among a plurality of other waiter prescription transactions in the work queue relative to the initial estimated pick up time or the computed reset estimated pick up time of the waiter prescription transaction.

7. The computer program of claim 1 wherein the drug prescription transaction includes a waiter prescription transaction including one or more prescriptions being processed for fulfillment while the customer waits for processing and fulfillment of such waiter prescription transaction.

8. The computer program of claim 7 comprising instructions for:

computing the initial estimated pick up time of the waiter prescription transaction including:

determining a total number of prescriptions in the waiter prescription transaction;

determining a total number of waiter prescriptions in the work queue within a first given period of time and identify the first given period of time as a first pick up time;

adding a percentage of a total number of non-waiter prescriptions in the work queue to the total number of waiter prescriptions in the work queue to determine a total number of prescriptions within a second period of time and identifying the second period of time as a second pick up time, wherein the non-waiter prescriptions include prescriptions being processed for fulfillment without customers waiting for the processing and fulfillment of the prescription transactions;

comparing the first pick up time and the second pickup time with a default pick up time, the default pick up time being a programmed maximum wait time stored in the computer system for a waiter prescription transaction, wherein if the first pick up time is less than the default pick up time, recording the first pick up time as the initial estimated pick up time, or if the first pick up time is less than the default pick up time and the second pick up time is more than the default pick up time, recording the default pick up time as the initial estimated pick up time, or if the first and the second pick up times are less than the default pick up time, recording the second pick up time as the initial estimated pick up time.

* * * * *